(12) United States Patent
Kirby et al.

(10) Patent No.: US 9,714,926 B2
(45) Date of Patent: Jul. 25, 2017

(54) COLUMN HEATER WITH ACTIVE PRE-HEATING

(71) Applicant: Waters Technologies Corporation, Milford, MA (US)

(72) Inventors: Peter Kirby, Derry, NH (US); Tony A. Lin, Ashland, MA (US); Steven D. Trudeau, Webster, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 6 days.

(21) Appl. No.: 15/249,720

(22) Filed: Aug. 29, 2016

(65) Prior Publication Data

US 2016/0363564 A1 Dec. 15, 2016

Related U.S. Application Data

(63) Continuation of application No. 13/519,818, filed as application No. PCT/US2011/020803 on Jan. 11, 2011, now Pat. No. 9,453,824.

(Continued)

(51) Int. Cl.
*G01N 30/30* (2006.01)
*F24H 1/14* (2006.01)
(Continued)

(52) U.S. Cl.
CPC ............. *G01N 30/30* (2013.01); *F24H 1/142* (2013.01); *G01N 30/54* (2013.01); *H05B 3/42* (2013.01);
(Continued)

(58) Field of Classification Search
CPC ........... G01N 30/30; G01N 2030/3046; G01N 2030/3053; G01N 2030/3061;
(Continued)

(56) References Cited

U.S. PATENT DOCUMENTS 3,213,596 A 10/1965 Gill
3,522,725 A 8/1970 Waters
(Continued)

FOREIGN PATENT DOCUMENTS

DE 3541641 A1 5/1987
DE 20304609 U1 6/2003
(Continued)

OTHER PUBLICATIONS

International Search Report and Written Opinion for counterpart international application No. PCT/US2011/020803 dated Mar. 29, 2011; 8 pages.
(Continued)

*Primary Examiner* — Jan Ludlow
(74) *Attorney, Agent, or Firm* — Schmeiser, Olsen & Watts LLP

(57) ABSTRACT

To heat a flowing liquid, an apparatus includes a heater block assembly having a heater block made of thermally conductive material. The heater block assembly has a tube inlet, a tube outlet, and a tube path between the tube inlet and tube outlet. Tubing extends through the tube path from the tube inlet to the tube outlet. The tubing is in thermal communication with the heater block. A heater cartridge, in thermal communication with the heater block, is configured to provide heat to the heater block for transfer to liquid flowing through the tubing between the tube inlet and the tube outlet of the heater block assembly. Circuitry is in electrical communication with the heater cartridge to control a temperature of the heater block by controlling operation of the heater cartridge.

10 Claims, 24 Drawing Sheets

Related U.S. Application Data

(60) Provisional application No. 61/293,917, filed on Jan. 11, 2010.

(51) Int. Cl.
*G01N 30/54* (2006.01)
*H05B 3/42* (2006.01)

(52) U.S. Cl.
CPC ............... *G01N 2030/3007* (2013.01); *G01N 2030/3061* (2013.01); *H05B 2203/021* (2013.01)

(58) Field of Classification Search
CPC ... G01N 2030/3069; G01N 2030/3076; G01N 2030/3084
See application file for complete search history.

(56) References Cited

U.S. PATENT DOCUMENTS

| | | | |
|---|---|---|---|
| 4,026,803 | A | 5/1977 | Abrahams et al. |
| 4,350,586 | A | 9/1982 | Conlon et al. |
| 5,032,283 | A | 7/1991 | Scott et al. |
| 5,393,239 | A | 2/1995 | Ursich |
| 5,601,707 | A | 2/1997 | Clay et al. |
| 5,983,710 | A | 11/1999 | Uhen et al. |
| 6,197,198 | B1 | 3/2001 | Messinger et al. |
| 6,442,341 | B1 | 8/2002 | Wu |
| 7,258,726 | B2 | 8/2007 | Ledford, Jr. |
| 7,326,893 | B2 | 2/2008 | Kanzaki et al. |
| 7,731,463 | B2 | 6/2010 | Davis et al. |
| 8,613,216 | B2 | 12/2013 | Vorm |
| 2003/0061867 | A1 | 4/2003 | Gerner et al. |
| 2006/0054558 | A1 | 3/2006 | Jones et al. |
| 2008/0277345 | A1 | 11/2008 | Prentice et al. |
| 2013/0277350 | A1 | 10/2013 | Arima |
| 2015/0135861 | A1 | 5/2015 | Cook |

FOREIGN PATENT DOCUMENTS

| | | |
|---|---|---|
| WO | 2010138678 A1 | 12/2010 |
| WO | 2011085359 A1 | 7/2011 |

OTHER PUBLICATIONS

International Search Report & Written Opinion for related International Patent Application No. PCT/US2013/025661 mailed Apr. 16, 2013, 8 pages.
International Preliminary Report on Patentability in related International Patent Application No. PCT/US2013/025661, mailed Sep. 18, 2014; 7 pages.
Partial Search Report in counterpart European Patent Application No. 11732307.1, mailed on Feb. 3, 2016; 8 pages.
International Preliminary Report on Patentability in counterpart International Patent Application No. PCT/US2011/020803, mailed Jul. 26, 2012; 8 pages.
Non-Final Office Action in related U.S. Appl. No. 14/381,383, mailed on May 18, 2016; 16 pages.
Extended European Search Report in counterpart European Patent Application No. 11732307.1, mailed on May 30, 2016; 13 pages.
Restriction and/or Election Requirement in counterpart U.S. Appl. No. 13/519,818, mailed on Apr. 8, 2015; 12 pages.
Non-Final Office Action in counterpart U.S. Appl. No. 13/519,818, mailed on Jul. 7, 2015; 13 pages.
Final Office Action in counterpart U.S. Appl. No. 13/519,818, mailed on Dec. 2, 2015; 10 pages.
Notice of Allowance and Fees Due in counterpart U.S. Appl. No. 13/519,818, mailed on Apr. 22, 2016; 8 pages.
Notice of Allowance and Fees Due in counterpart U.S. Appl. No. 13/519,818, mailed on May 23, 2016; 12 pages.
Notice of Allowance in related U.S. Appl. No. 14/381,383, mailed on Sep. 23, 2016; 7 pages.

COLUMN HEATER WITH ACTIVE PRE-HEATING

RELATED APPLICATIONS

This application is a continuation patent application of U.S. patent application Ser. No. 13/519,818, filed Aug. 22, 2012, which is the national stage of International Application No. PCT/US2011/020803, filed Jan. 11, 2011, which claims benefit of and priority to U.S. Provisional Patent Application No. 61/293,917, filed Jan. 11, 2010. The contents of these applications are expressly incorporated herein by reference in their entireties.

FIELD OF THE INVENTION

The invention relates generally to liquid chromatography systems. More specifically, the invention relates to controlling temperature of columns used in liquid chromatography systems.

BACKGROUND

Chromatography is a set of techniques for separating a mixture into its constituents. Generally, in a liquid chromatography analysis, a pump system takes in and delivers a mixture of liquid solvents (and/or other fluids) to a sample manager, where a sample awaits injection into the solvents. The sample is the material under analysis. Examples of samples include complex mixtures of proteins, protein precursors, protein fragments, reaction products, and other compounds, to list but a few. In an isocratic chromatography application, the composition of the liquid solvents remains unchanged, whereas in a gradient chromatography application, the solvent composition varies over time. The mobile phase, comprised of a sample dissolved in a mixture of solvents (and/or other fluids), moves to a point of use, such as a column, referred to as the stationary phase.

By passing the mobile phase through the column, the various components in the sample separate from each other at different rates and thus elute from the column at different times. A detector receives the separated components from the column and produces an output from which the identity and quantity of the analytes may be determined. Temperature can influence the results of the analysis, affecting such properties as the separation performance of the column and the viscosity of a mobile phase. Therefore, maintaining an accurate constant column temperature is important to the accuracy and reproducibility of the results.

SUMMARY

In one aspect, the invention features an apparatus for heating a liquid in a liquid chromatography system. The apparatus includes a heater block assembly, tubing, a heater cartridge, a chromatography column and circuitry. The heater block assembly includes a heater block made of thermally conductive material. The heater block assembly has a tube inlet, a tube outlet, and a tube path between the tube inlet and the tube outlet. The tubing extends through the tube path from the tube inlet to the tube outlet and is in thermal communication with the heater block. The heater cartridge is in thermal communication with the heater block and is configured to provide heat to the heater block for transfer to liquid flowing through the tubing between the tube inlet and the tube outlet of the heater block assembly. The chromatography column is coupled to an end of the tubing that emerges from the tube outlet of the heater block assembly. The circuitry is in electrical communication with the heater cartridge and controls a temperature of the heater block by controlling operation of the heater cartridge.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Figure 1:
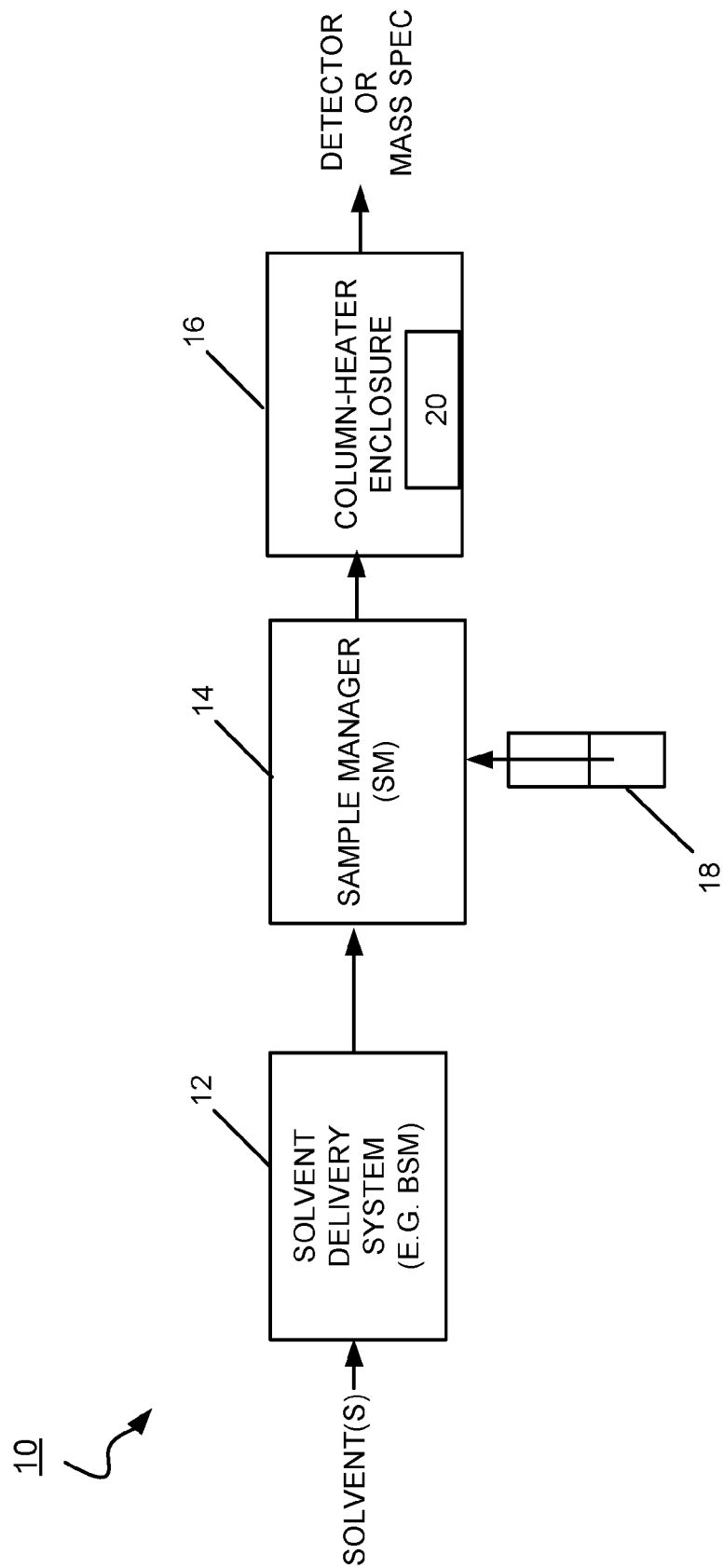
FIG. 1 is a functional block diagram of an embodiment of a liquid chromatography system including a column-heater enclosure having a thermal module with an active pre-heater assembly.

Systems described herein include a column-heater enclosure for controlling temperature of a chromatographic column during liquid chromatography analyses. Temperature control of the column and of the liquid flowing into the column is an important contributor to producing consistent and reliable results. Various embodiments of these systems relate to liquid-chromatography apparatus, for example, HPLC (High Performance Liquid Chromatography) and UPLC (Ultra Performance Liquid Chromatography) systems. The column-heater enclosure has a detachable thermal module, which provides a temperature-controlled environment for one or more columns and liquid pre-heating, as described herein. Being able to remove the thermal module facilitates ease of maintenance.

In some configurations, the thermal module is disposed at the front of the column-heater enclosure. In other configurations, the thermal module is attached to a special hinge bracket mounted at the front of the column-heater enclosure. This bracket enables the thermal module to be positioned to one side of the column-heater enclosure. Thus, if equipment, such as a mass spectrometer, is to be located either on one side of or in front of the column-heater enclosure, the thermal module can be moved into proximity of the equipment or moved away from the front of the column-heater enclosure to make room for the equipment.

Some embodiments of the thermal module include an active pre-heater assembly for pre-heating a flowing liquid before the liquid enters the column. In brief overview, the active pre-heater assembly includes a heater block made of thermally conductive material. Liquid flows through tubing that extends through a tube path in thermal communication with the heater block. Also in thermal communication with the heater block is a heater cartridge. The thermally conductive heater block transfers the heat generated by the heater cartridge to the liquid flowing through the tubing. The pre-heater assembly can include a temperature sensor for measuring the temperature of the heater block. Circuitry in electrical communication with the temperature sensor and with the heater cartridge actively controls the temperature of the heater block by controlling operation of the heater cartridge. In one embodiment, the active pre-heater assembly includes fittings for making a fluidic connection with the liquid chromatography column at one end and a fluidic connection with a sample manager at its opposite end.

In addition, the active pre-heater assembly is configured to plug into either of two electrical sockets of the thermal module. The electrical sockets are disposed at opposite ends of a trough compartment in the thermal module, such that there is an electrical socket on either side of a column residing within a trough in the trough compartment. Because the active pre-heater assembly sits upstream of the column, the particular electrical socket used determines the direction of flow of the liquid through the trough compartment. In addition, the ability to plug the active pre-heater assembly into either electrical socket, in conjunction with the ability to swing the thermal module away from the face of the column-heater enclosure, advantageously provides flexibility when setting up the various pieces of equipment related to a liquid chromatography apparatus.

FIG. 1 shows an embodiment of a liquid chromatography system 10 for separating a sample into its constituents. The liquid chromatography system 10 includes a solvent delivery system 12 in fluidic communication with a sample manager 14. Generally, the solvent delivery system 12 includes pumps (not shown) in fluidic communication with solvent reservoirs from which the pumps draw solvents. The solvent delivery system 12 delivers a mixture of solvents to the sample manager 14. The sample manager 14 is in fluidic communication with a sample source 18 from which the sample manager acquires and introduces a sample to the solvent mixture arriving from the solvent delivery system 12.

In fluidic communication with the sample manager 14 is a column-heater enclosure 16 for receiving therefrom the solvent composition containing the sample. The column-heater enclosure 16 includes a thermal module 20 for providing a controlled temperature environment for a liquid chromatography column used in separating sample-solvent compositions. As described herein, the thermal module 20 includes an active pre-heater assembly for controlling the temperature of the fluidic sample composition before it enters the column. From the column-heater enclosure 16, the constituents of the separated sample pass to a detector or other equipment, for example, a mass spectrometer, for analyzing the separation. In one embodiment, the liquid chromatography system 10 is a modified ACQUITY UPLC System the ACQUITY UPLC system available from Waters Corporation of Milford Mass.

Figure 2:
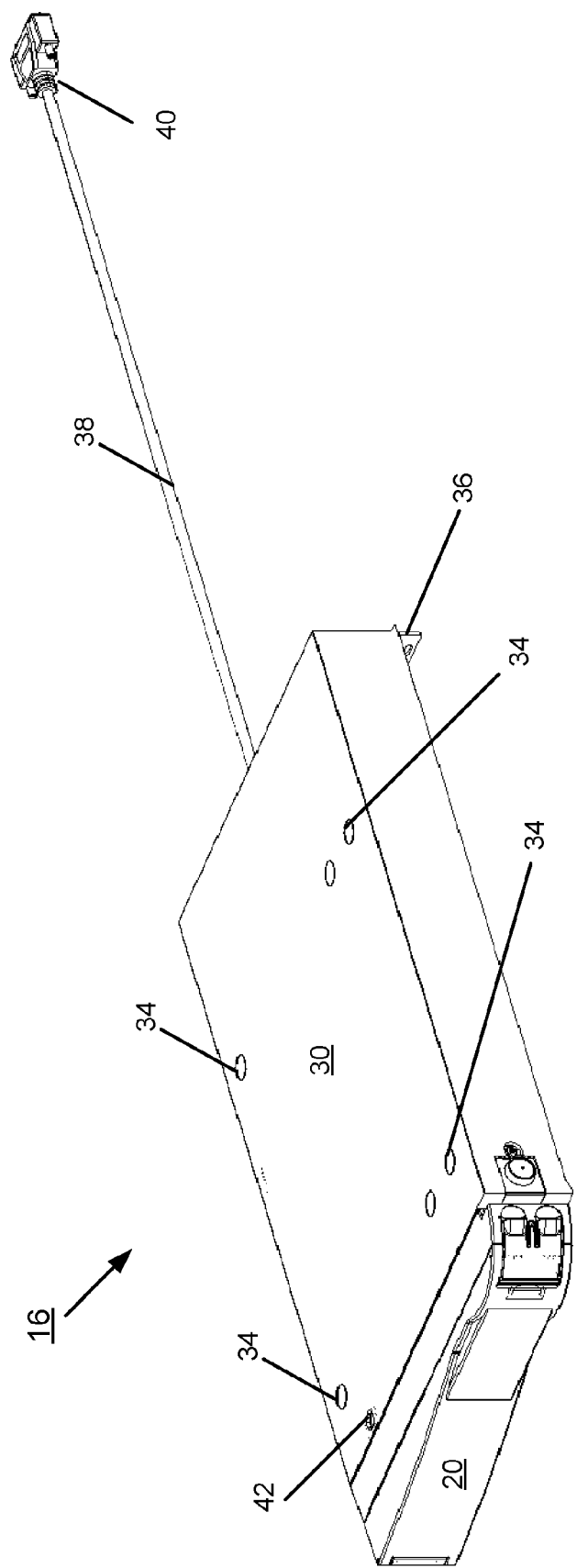
FIG. 2 is an isometric view of an embodiment of the column-heater enclosure with the thermal module.

FIG. 2 shows an embodiment of the column-heater enclosure 16 including the thermal module 20, which is attached to a front side of a main housing 30. In one embodiment, the housing 30 is 21.1 inches in length, 13.5 inches in width, and 3.5 inches in height.

Typically, the pieces of equipment, namely the solvent delivery system 12, solvent manager 14, and column-heater enclosure 16, can be vertically stacked. Such an arrangement can help shorten the length of the plumbing between the pieces of equipment. Other pieces, for example, mass spectrometers, because of their size, are often placed to one side of or in front of an equipment stack. Optionally, to accommodate the location of a mass spectrometer, a hinge bracket (FIG. 17-FIG. 20) can be mounted between the main housing 30 and the thermal module 20. Attached to this hinge bracket, the thermal module 20 can thus be positioned to one side of the main housing 30 in order to be brought into proximity of the mass spectrometer if located on one side of the column-heater enclosure 16 or to make room for the mass spectrometer if placed in front of the column-heater enclosure 16.

A role of the main housing 30 is to provide support for another piece of equipment, such as a detector, placed on top of the column-heater enclosure 16. The top surface of the housing 30 has dimples 34, for receiving the feet of the enclosure situated above. The dimples 34 align with structural columns within the housing 30 that support the borne weight. The column-heater enclosure 16, itself, can sit physically atop another piece of equipment, such as the sample manager 14. A flange 36 with openings for mechanical fasteners extends orthogonally from the base of the housing 30 and is for mounting the column-heater enclosure 16 securely to the sample manager 14 situated below. An electrical cord 38 and connector 40 electrically connect the column-heater enclosure 16 to the sample manager 14, from which the column-heater enclosure 16 receives DC power and communications for running the thermal module 20.

Another role of the housing 30 is to provide a fluid leakage path between the equipment sitting atop the column-heater enclosure 16 and the equipment sitting below. For this role, the top surface of the housing 30 has a drainage inlet 42, which connects to a drainage outlet of the upper equipment. An internal fluidic conduit (not shown) runs from the drainage inlet 42 to an outlet (not shown) in the bottom of the housing 30; and this outlet connects to an inlet of the lower equipment.

Figure 3:
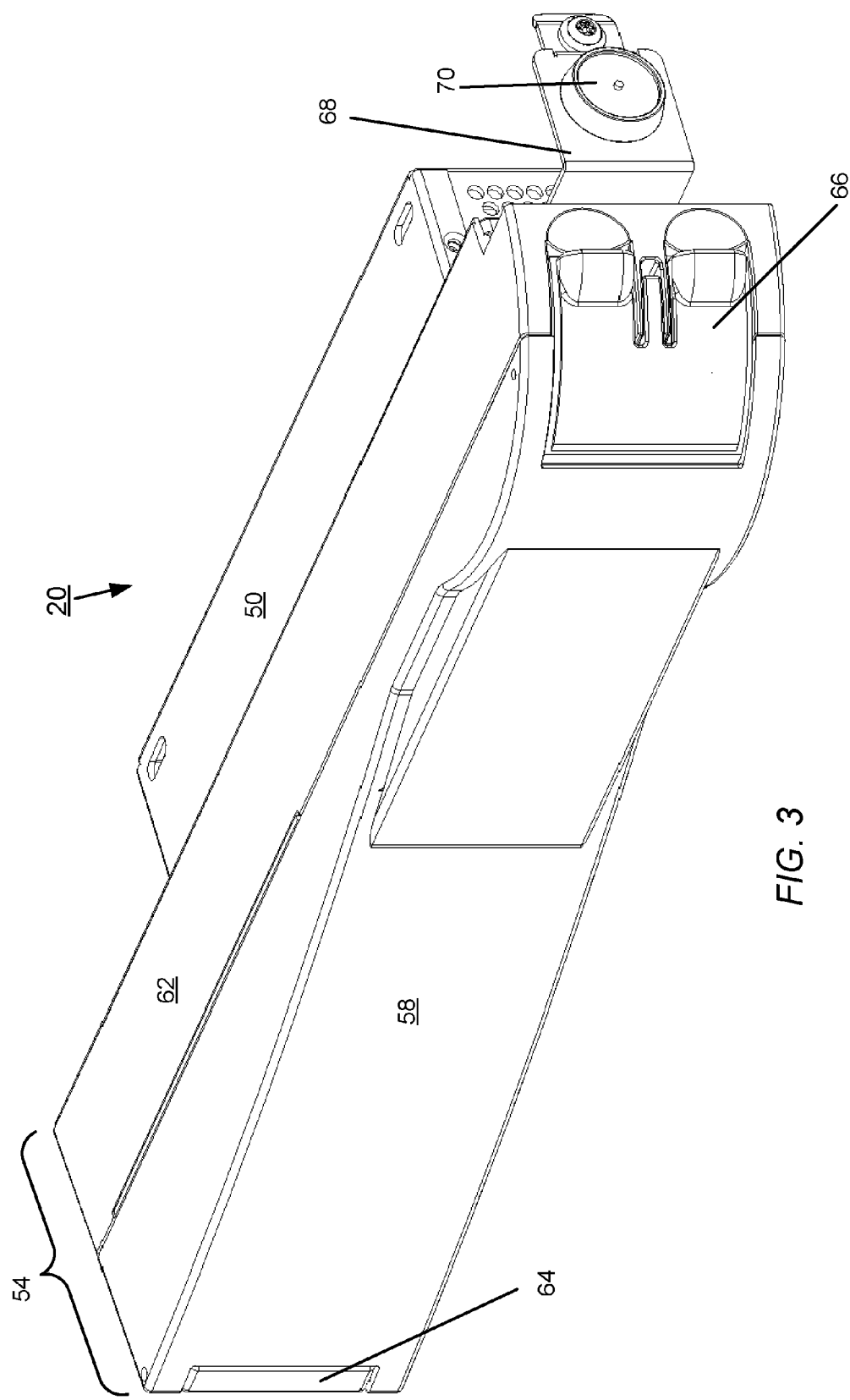
FIG. 3 is an isometric view of the thermal module.

FIG. 3 shows an embodiment of the thermal module 20 including an electronics housing 50 coupled to a column housing 54. The column housing 54 comprises a front door 58 coupled at one end to a column holder 62 by a hinge 64 and, at its opposite end, secured in a closed position to the column holder 62 by a (preferably mechanical) latch 66. A bracket 68 extends from one side of the electronics housing 50. The bracket 68 and electronics housing 50 can be made from a single piece of sheet metal. An electrical device 70 is mounted on a surface of the bracket 68. The device 70 is in electrical communication with electronics within the electronics housing 50 and is used to read identification information from some types of chromatography columns.

Figure 4:
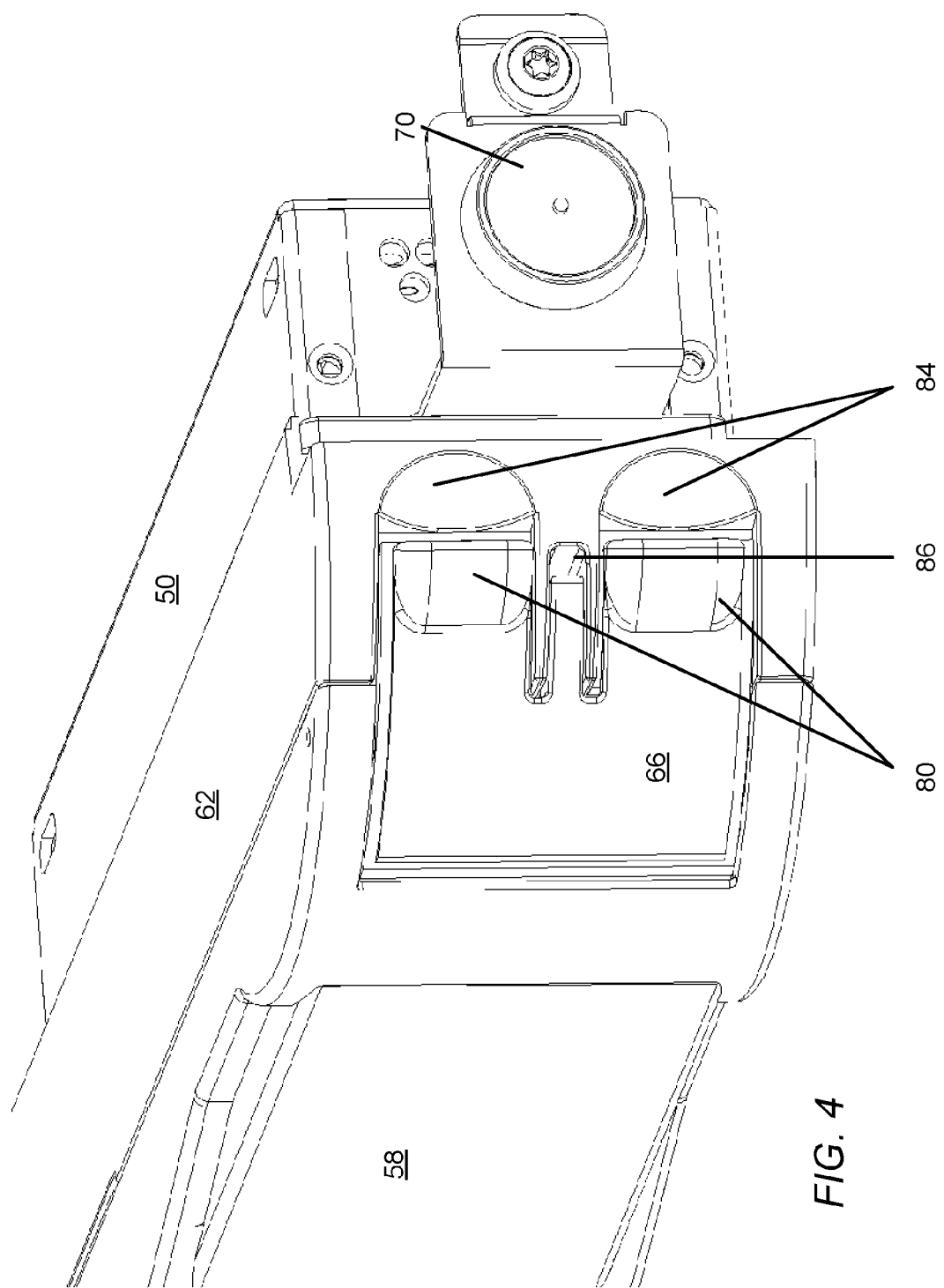
FIG. 4 is an end view of the thermal module with its door latched closed.

FIG. 4 shows an end view of the thermal module 20 with the latch 66. The latch 66 includes a pair of raised bumps 80. A curved side of each raised bump 80 extends from the surface of the latch; a planar side of each raised bump 80 provides an edge by which a human fingertip may pull upon the latch 66 in order to detach the door 58 from the column holder 62. A pair of recesses 84 at the latch end of the column holder 62 accommodates the fingertips that pull upon the raised bumps 80. With the door 58 in a closed position, a small gap 86 provides a passage for tubing into the column holder 62.

Figure 5:
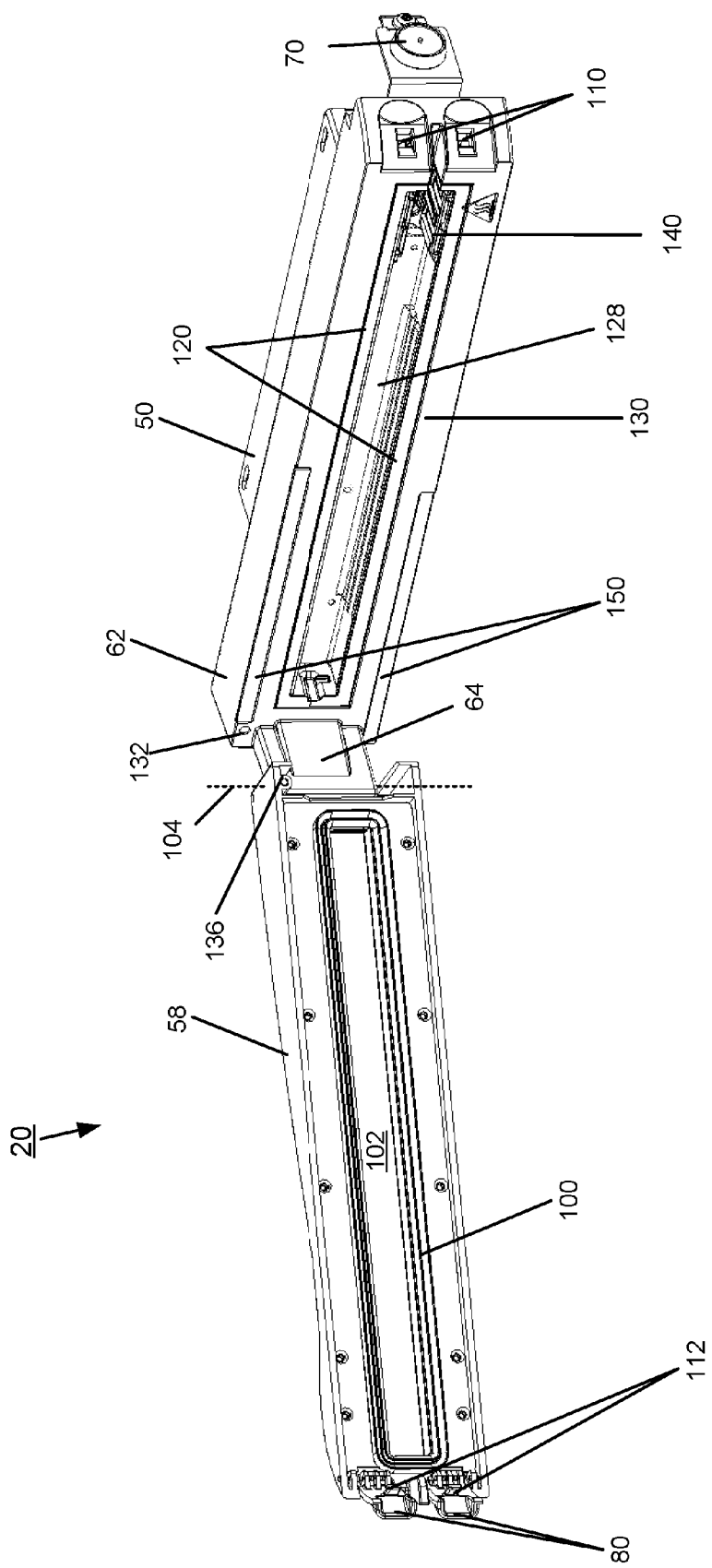
FIG. 5 is an isometric view of the thermal module with its door open.

FIG. 5 shows an isometric view of the thermal module 20 with its front door 58 open to reveal an interior side of the door 58 and the interior of the column holder 62. The interior side of the front door 58 has a generally rectangular rubber gasket 100 disposed near the door's edges. A layer of insulation 102 covers the door interior. A plastic panel (not shown) can be placed over this exposed insulation 102. The door 58 is attached at one end to the hinge 64 for pivoting about axis 104 between an open and closed position. The hinge 64 extends generally orthogonally from a front face 130 of the column holder 62 at one end thereof (opposite the latch end). At the opposite (latch) end of the column holder 62 are a pair of holes 110 for receiving corresponding latch elements 112 on the door 58. These latch elements 112 are interior-side extensions from the raised bumps 80 (FIG. 4) of the door latch 66 which are unlatched from the holes 110 when pulled upon by a person's fingertips.

The interior of the column holder 62 has an open-faced trough compartment 120, within which is a slidable trough 128. The trough 128 has a back surface and two opposing side surfaces. (The door 58, when closed, provides a fourth side for enclosing the trough compartment 120, the gasket 100 on the door interior pressing against the front face 130 and providing a tight thermal seal around the trough compartment 120.) This trough 128 can be slid to either end of the trough compartment 120, as deemed appropriate when configuring the thermal module 20 for use. Here, the slidable trough 128 is shown positioned at the end of the trough compartment 120 near the hinge 64. At the other end of the trough compartment 120 is a receptacle 140 for receiving an active pre-heater assembly, as describe in more detail below.

The front face 130 of the column holder 62 has a magnetic switch 132 located at the hinge end of the thermal module 20. The magnetic switch 132 detects when a connection is broken between the switch 132 and an opposing magnet 136 on the door 58 (i.e., when the door opens). The thermal module 20 uses signals from the magnetic switch 132 to determine whether to maintain or disconnect power to an active pre-heater assembly installed within the column holder 62.

Also near the hinge end of the thermal module, the front face 130 has two rubber gasket strips 150 at the top and bottom edges of the column holder 62. The regions of the front face 130 where the gaskets 150 reside are slightly indented so that the surface of each gasket 150 is on substantially the same plane as the rest of the front face 130 of the column holder 62; that is, when closed, the door 58 presses flush against the gaskets 150 and the front face 130, with little, if any, deformation of the gaskets 150. The resilient, pliable nature of the gaskets 150 avoids pinching the tubing that enters or exits, by way of either the top edge or bottom edge, at the hinge end of the thermal module 20.

Figure 6:
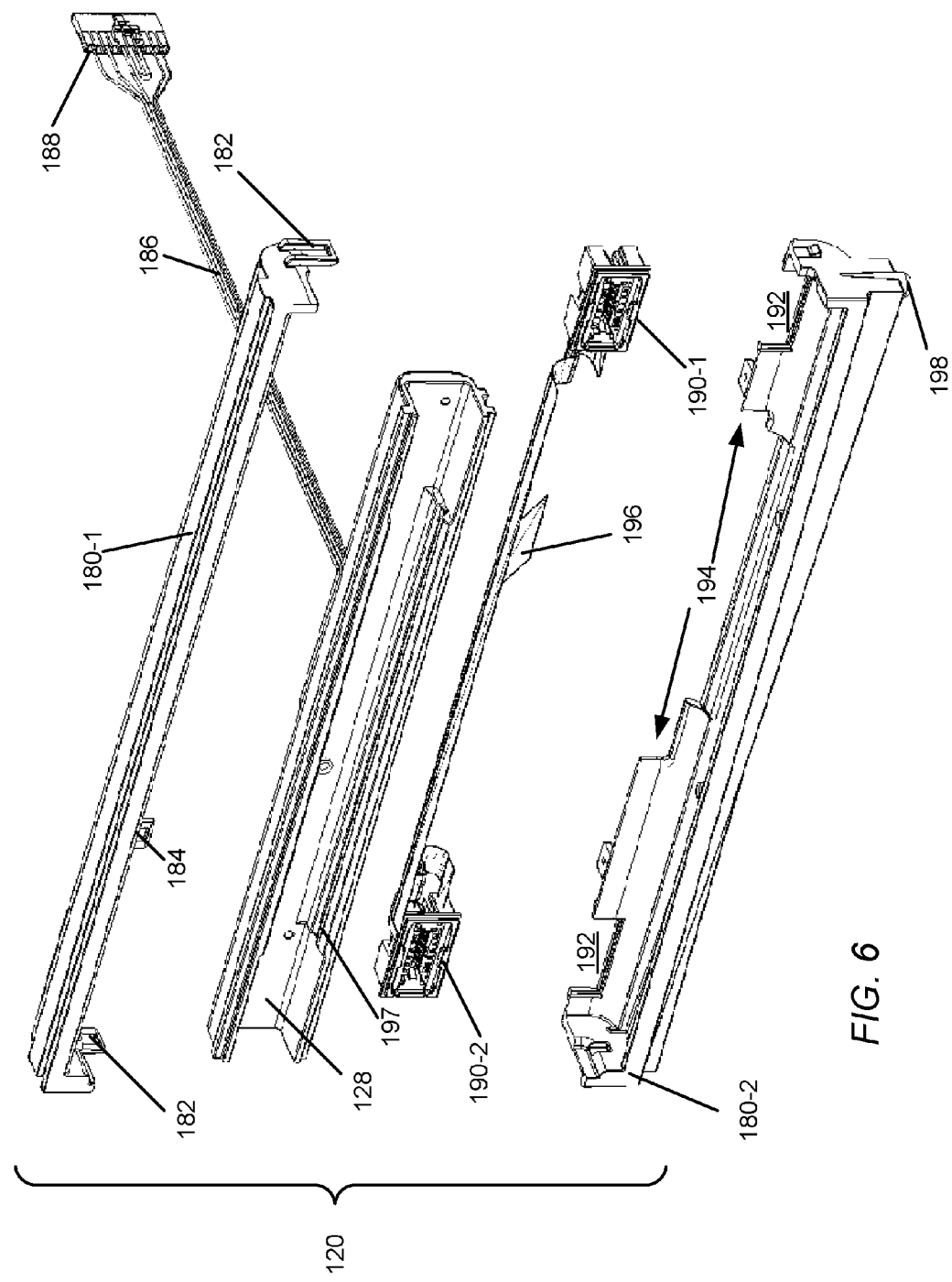
FIG. 6 is an exploded view of a trough compartment within the thermal module.

FIG. 6 shows an exploded view of the trough compartment 120 of the column holder 62. The trough compartment 120 is made of two halves 180-1, 180-2 (generally, 180) held together by two end snaps 182 and a rear snap 184. Mechanical fasteners may also be used to hold the two halves 180 together. Disposed between the two halves 180 is the trough 128 and a pair of electrical sockets 190-1, 190-2 (generally 190) used for electrical connection to an active pre-heater assembly. The sockets 190 sit in appropriately sized rectangular cutout regions 192 in the lower half 180-2 of the trough compartment 120. An electrical ribbon cable 196 is connected between each electrical socket 190 and the electronics within the electronics housing 50 (FIG. 3). The trough 128 can slide to either end of the trough compartment 120 to cover one of the electrical sockets 190.

An electrical cable 186 extends from a rear side of the trough 128 to an electrical connector 188, which plugs into electronics within the housing 50. The electrical cable 186 carries electrical signals for controlling a heater (not shown) and temperature sensor (not shown) mounted to the rear side of the trough 128. The heater is used to heat the trough 128 and the temperature sensor measures temperature of the trough 128. A back surface of the lower half 180-2 of the trough compartment 120 has cutout region 194 to accommodate the cable 186 when the trough 128 slides from one end of the compartment 120 to the other. In addition, the trough 128 has a groove 197, which serves to channel any leakage into the lower half 180-2 of the trough compartment 120.

Extending from the bottom at one end of the lower half 180-2 is a spout 198 for providing a fluidic drainage path for leakage or condensation within the trough 128, the bottom of the lower half 180-2 being sloped towards the spout 198. For example, any condensation forming on the door interior drips into the trough 128 and out through the spout 198.

Figure 7:
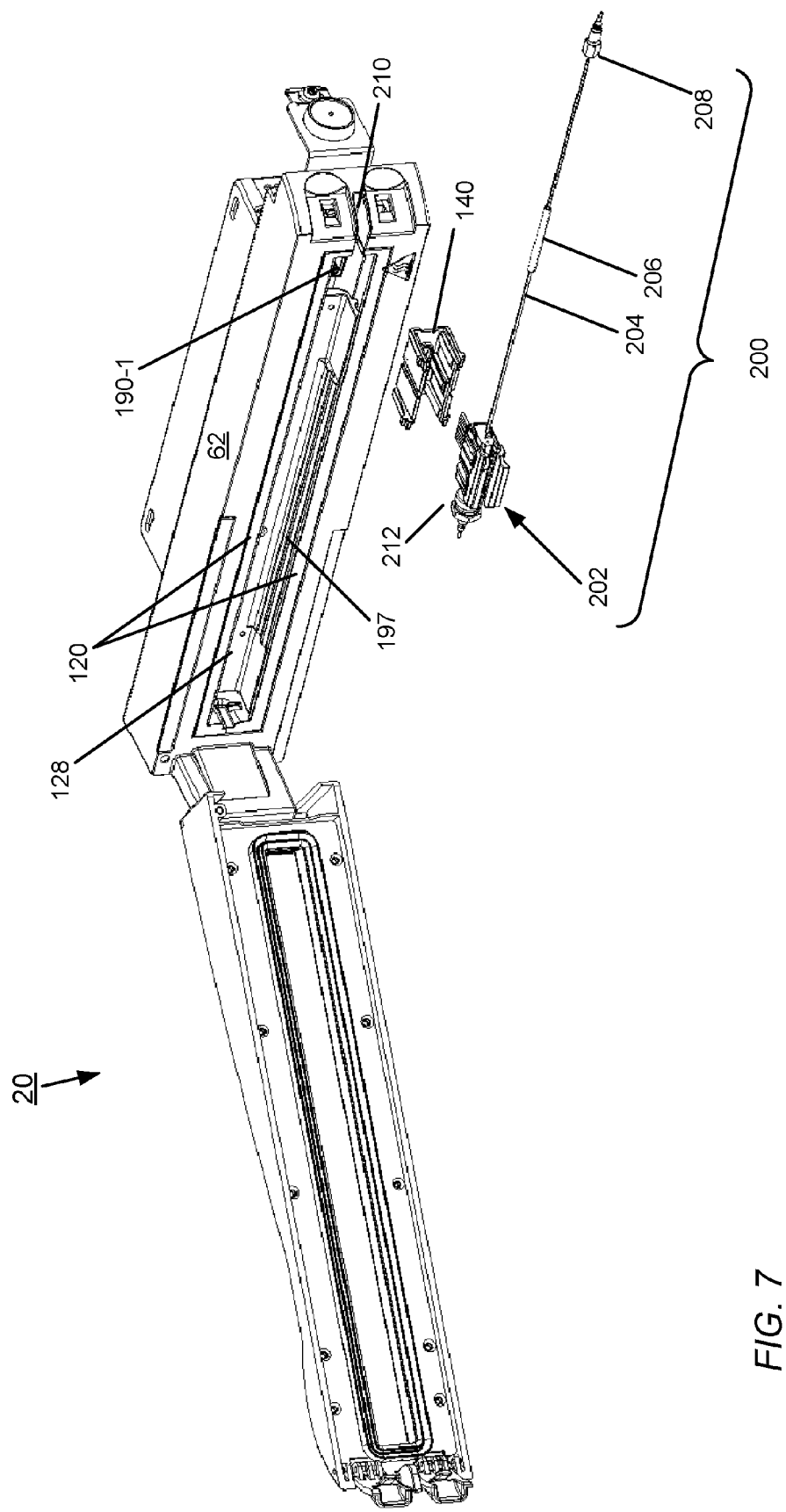
FIG. 7 is an isometric view of a first configuration of the thermal module, including a view of the active pre-heater assembly disposed at a latch end of the thermal module.

FIG. 7 shows an isometric view of the thermal module 20 in a first configuration. The front door 58 of the thermal module is open. An exploded view shows an active pre-heater assembly 200 to include a main heater block assembly 202 with tubing 204 extending from one side thereof. In general, the pre-heater assembly 200 heats liquid before the liquid reaches the column (not shown) residing in the trough 128. In one embodiment, the range of temperatures produced by the pre-heater assembly is approximately 4° to 100° C.

Tubing 204 fluidically connects the pre-heater assembly 200 to the sample manager (not shown) for receiving a sample-solvent composition therefrom. A tube sleeve 206 is shrink-wrapped around a section of the tubing 204. Tube fittings 208 are for connecting one end of the tubing 204 to an outlet port the sample manager. Column fittings 212 are for connecting the other end of the tubing 204 to a liquid chromatography column (not shown) disposed within the trough 128.

In the first configuration, the trough 128 in the trough retainer 120 covers the socket 190-2 (FIG. 6) and leaves the other socket 190-1 exposed. The plastic receptacle 140 is shown aligned with the socket 190-1, where the receptacle 140 snaps into the trough compartment 120. The heater block assembly 202 is shown aligned with the receptacle 140, into which the heater block assembly 202 snaps. When the pre-heater assembly 200 is installed in the trough compartment 120, the tubing 204 passes through a slit 210 in the latch side of the column holder 62.

Figure 8:
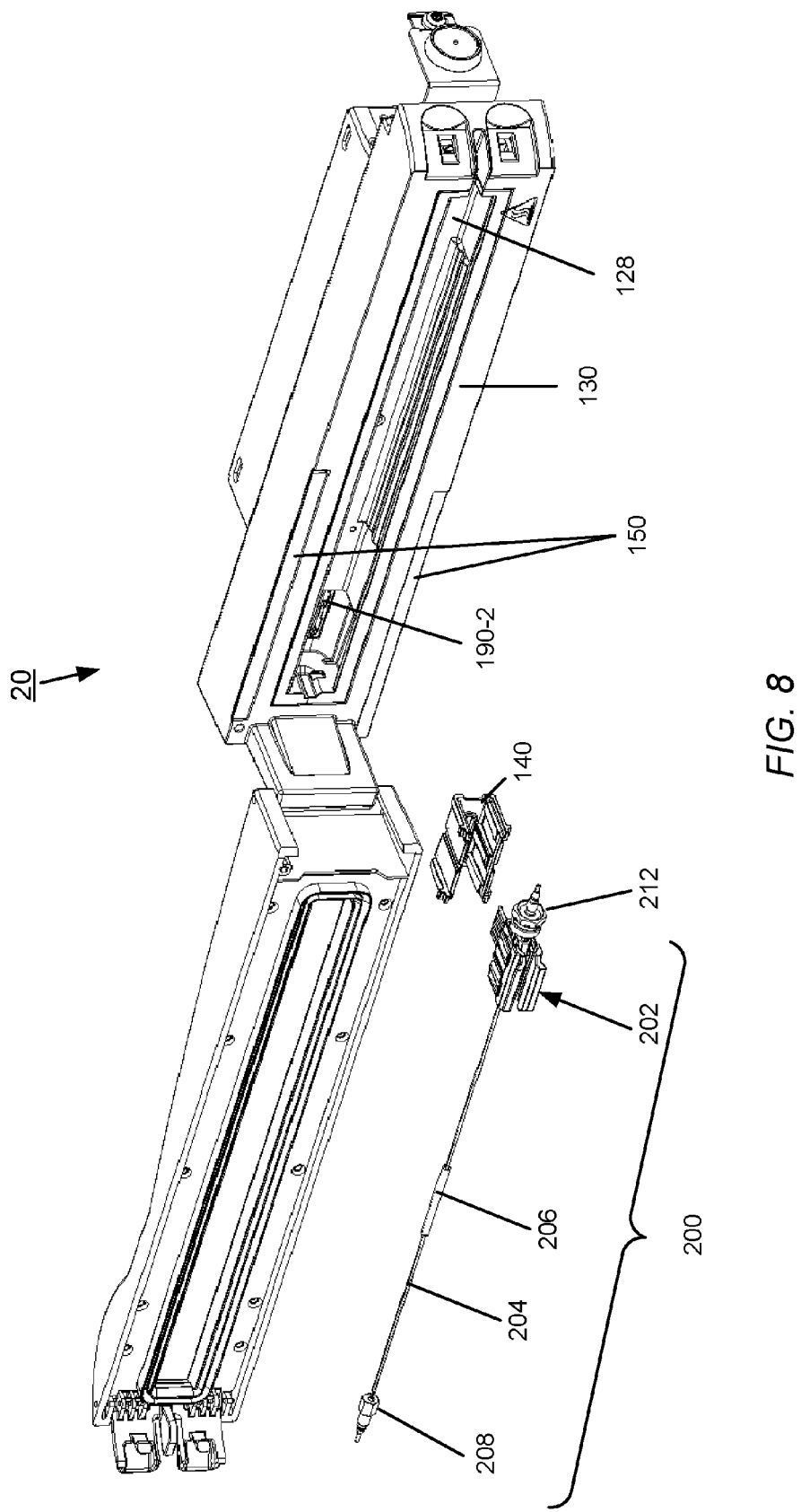
FIG. 8 is an isometric view of a second configuration of the thermal module, including a view of the active pre-heater assembly disposed at a hinge end of the thermal module.

FIG. 8 shows an isometric view of the thermal module 20 in a second configuration. Again, the front door 58 is open and shown is the active pre-heater assembly 200. In this configuration, the trough 128 is slid toward the latch end of the trough compartment 120, where it covers the socket 190-1 (FIG. 7), and leaves exposed the socket 190-2 at the hinge end of the trough compartment 120. The receptacle 140 is in alignment with the socket 190-2, positioned for snapping into the trough compartment 120 at that location. The heater block assembly 202 is aligned for snapping into the receptacle 140. In reverse orientation of that shown in FIG. 7, the pre-heater assembly 200 is configured such that the column fittings 212 extend in the direction of the latch end of the trough compartment 120, whereas the tube fittings 208 extend in the direction of the hinge end. Although the tubing 204 is shown extending straight past the door 58, in practice, the tubing 204 either bends upwards over the gasket 150 at the upper edge of the compartment front face 130 or downwards over the gasket 150 at the lower edge. The direction of liquid flow in the second configuration is opposite that in the first configuration.

Figure 9:
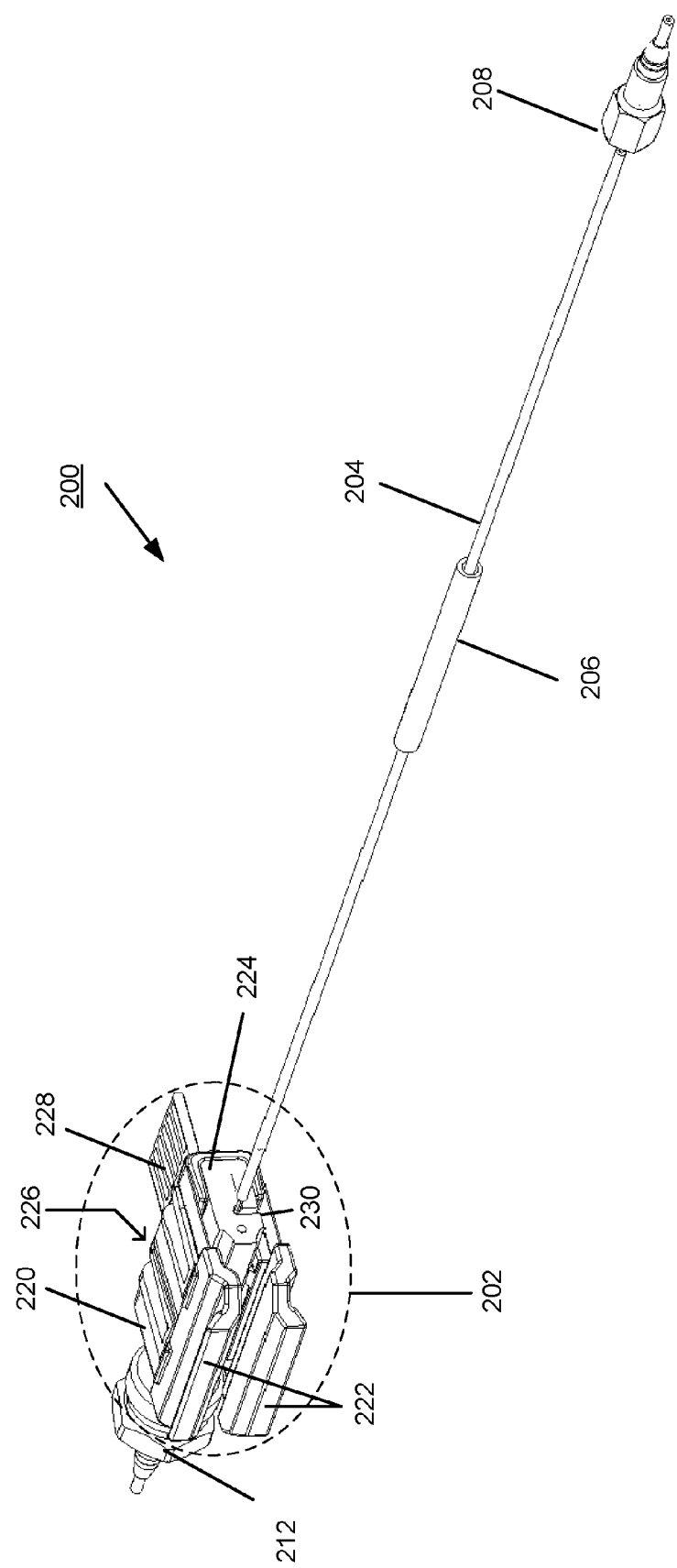
FIG. 9 is an isometric view of an embodiment of the active pre-heater assembly including a heater block assembly with tubing, tube fittings, and column fittings.

FIG. 9 shows an isometric view of an embodiment of the active pre-heater assembly 200 including the heater block assembly 202, tubing 204, a tube sleeve 206 shrink-wrapped around a section of the tubing 204, tube fittings 208, and column fittings 212. The heater block assembly 202 comprises a spring carrier 220 made of a pair of opposing prongs 222 spaced apart by a rear wall 226, a heater block 224 disposed between the prongs 222, and a printed circuit board 228 extending from a reverse side of the rear wall 226. The tubing 204 passes into a channel 230 in one side of the heater block 224. The active pre-heater assembly 200 can be constructed as a single inseparable unit or as multiple separable components that snap together.

Figure 10A:
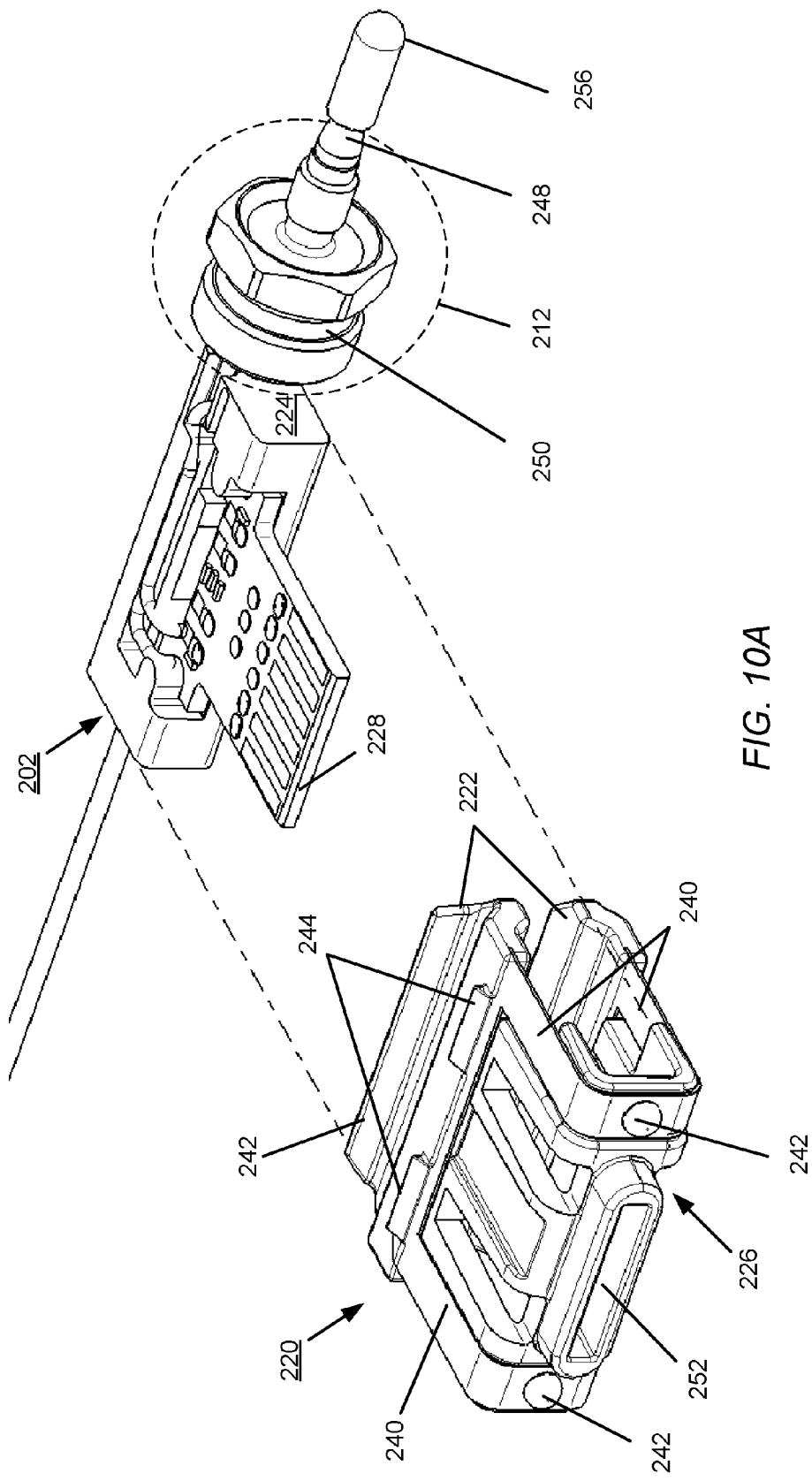
FIG. 10A is an exploded reverse view of the active pre-heater assembly of FIG. 9.
Figure 10B:
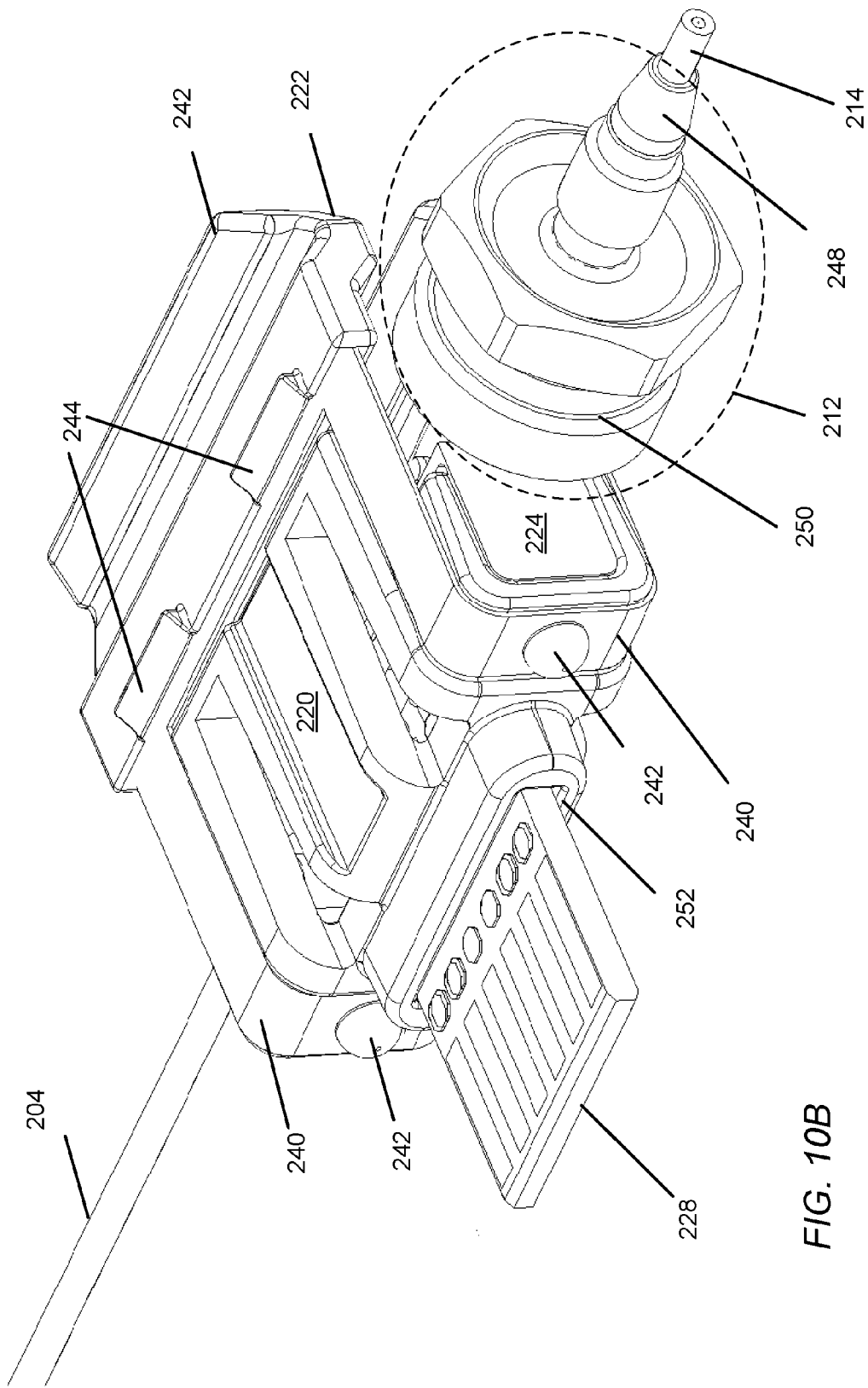
FIG. 10B is a reverse view of the active pre-heater assembly of FIG. 9

FIG. 10A and FIG. 10B are reverse views of the active pre-heater assembly 200: FIG. 10A shows the heater block assembly 202 aligned for coupling to the spring carrier 220 and FIG. 10B shows the heater block assembly 202 joined to the spring carrier 220. The opposing prongs 222 of the spring carrier 220 are integrally formed with a metallic leaf-spring 240. The leaf-spring 240 is a flat, rectangular window of metallic material that is curved into an arcuate shape defined by the prongs 222. The leaf-spring 240 biases the prongs 222 of the spring carrier 220 apart and bends when the prongs 222 are pinched together.

The leaf-spring 240 has openings through which project molded posts 242, which are melted to hold the leaf-spring 240. Each prong 222 of the spring carrier 220 has a pair of raised ramps 244 that snap into openings in interior surfaces of the receptacle 140 (FIG. 8). A raised edge 242 of each prong 222 provides a finger grip that a user can use to pinch the prongs 222 together in order to decouple the ramps 244 from the receptacle 140 so that the spring carrier 220 can be removed. The printed circuit board 228 of the heater block assembly 202 is aligned to project through a rear side opening 252 in the rear wall 226 of the spring carrier 220.

In one embodiment, the column fittings 212 include a ferrule 248, slipped over the tubing 204, and an adjustable biasing element 250 for urging the ferrule 248 and the tip of the tubing 204 (here, with a shipping cap 256 to be removed upon installation) into a corresponding inlet port of the liquid chromatography column.

Figure 11:
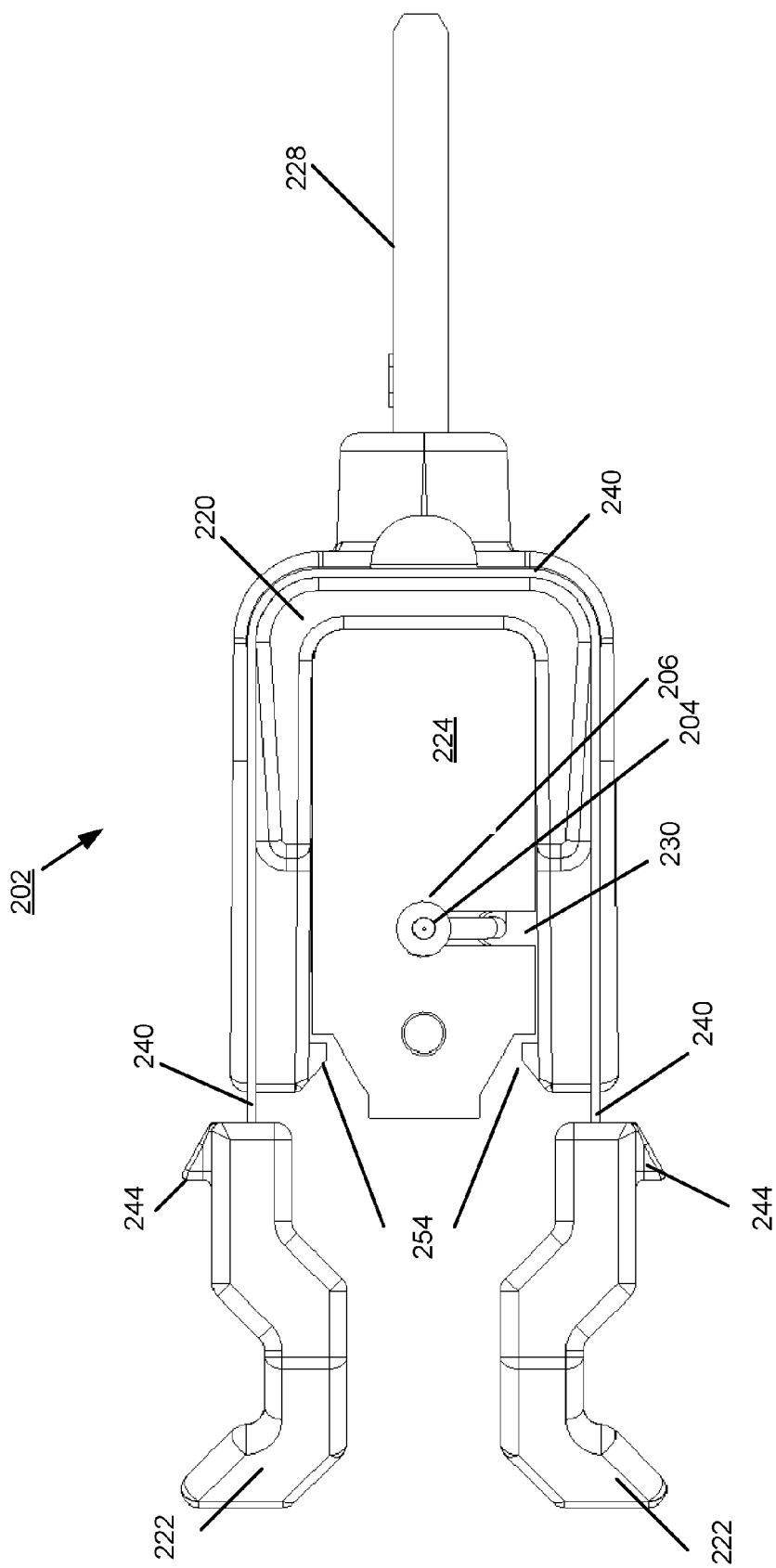
FIG. 11 is a side view of the heater block assembly.

FIG. 11 shows a side view of the heater block assembly 202 of the active pre-heater assembly 200 with the heater block 224 disposed between the prongs 222 of the spring carrier 220 and being held in place by snap features 254 extending from an interior surface of the prongs 222. Hardware is omitted from FIG. 11 for clarity. The heater block 224 is made of aluminum or of some other thermally conductive alloy.

Figure 12:
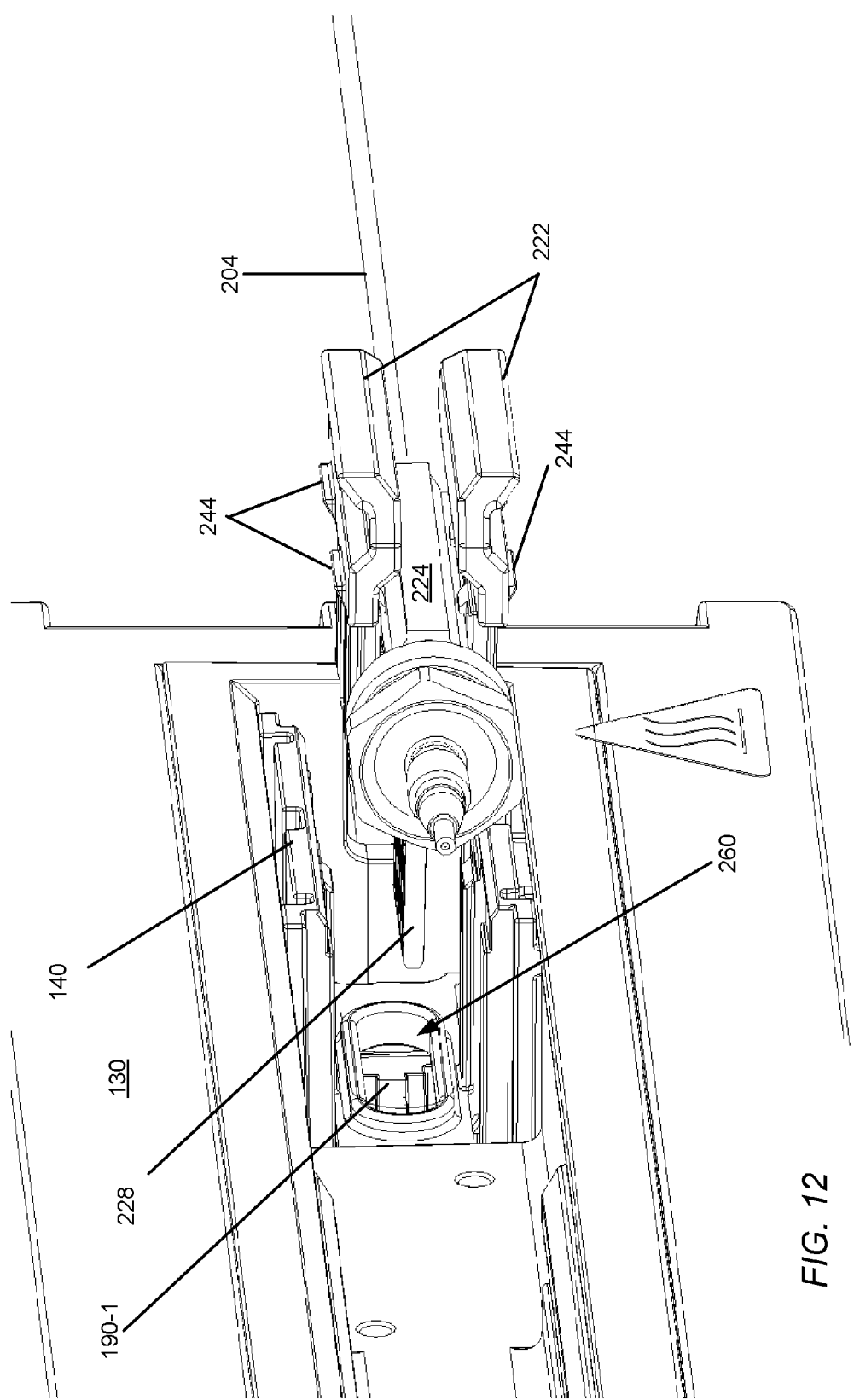
FIG. 12 is side view of the active pre-heater assembly positioned to enter a receptacle installed within the trough compartment.

FIG. 12 shows an exploded view of the active pre-heater assembly 200 positioned for insertion into the receptacle 140, which is here installed in front of the socket 190-1 of the trough compartment 120 of the column holder 62. The circuit board 228 is aligned for entry into an opening 260 in the crook of the receptacle 140. When the pre-heater assembly 200 is fully installed, the circuit board 228 penetrates this opening 260 and plugs into the electrical socket 190-1 situated behind the receptacle 140.

Figure 13:
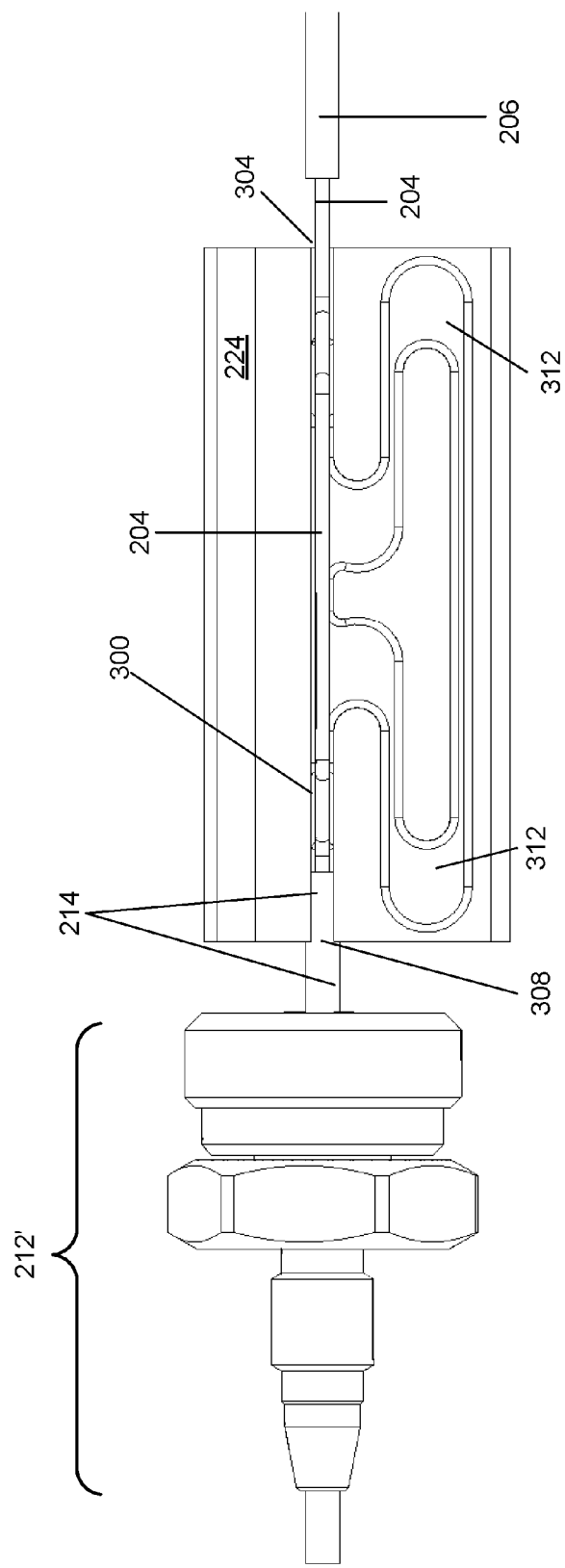
FIG. 13 is a side view of the heater block with two different embodiments of tube paths extending therethrough.

FIG. 13 shows a top view of one embodiment of the heater block 224 with two alternative embodiments of channels or tube paths extending therethrough. The heater block 224 can be constructed with either or both tube paths. During fabrication, the tubing 204 is soldered into one of the tube paths, placing the tubing 204 in thermal communication with the heater block 224. One of the tube paths is a straight direct path 300 between a tube inlet 304 and a tube outlet 308. The straight path 300 minimizes chromatography sample dispersion. A second tube path is a serpentine path 312 between the tube inlet 304 and the tube outlet 308. In one embodiment, the serpentine path 312 provides a 2-inch fluidic path through the heater block 224. This length has been found to enable the pre-heater assembly to heat water flowing at 2 mls per minute, through tubing having an approximately 0.004-inch inner diameter, from 4° C. to 90° C. FIG. 13 shows the tubing 204 passing through the direct path 300.

A metal tube sleeve 214 is welded around the tubing 204 and extends partially into the heater block 224 at the tube outlet 308, where the tube sleeve 214 is bonded to the heater block 224 to provide strain relief. The tube sleeve 214 can also pass completely through and project from the column fittings 212.

Figure 14:
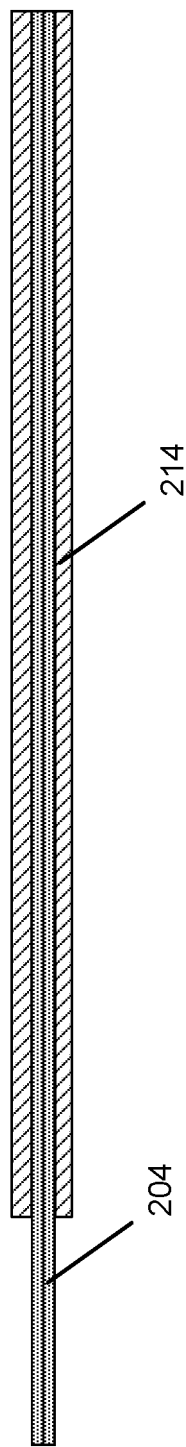
FIG. 14 is a cross-section side view of tubing and tube sleeve of the pre-heater assembly.

FIG. 14 shows a cross-section side view of one embodiment of the tubing 204 with the metal tube sleeve 214. In one embodiment, the tubing 204 has an inside diameter of approximately 0.011 inches or less and an outside diameter (OD) of approximately 0.025 inches or less. The outer diameter of the metal tube sleeve 214 is approximately 0.063 inches.

Figure 15A:
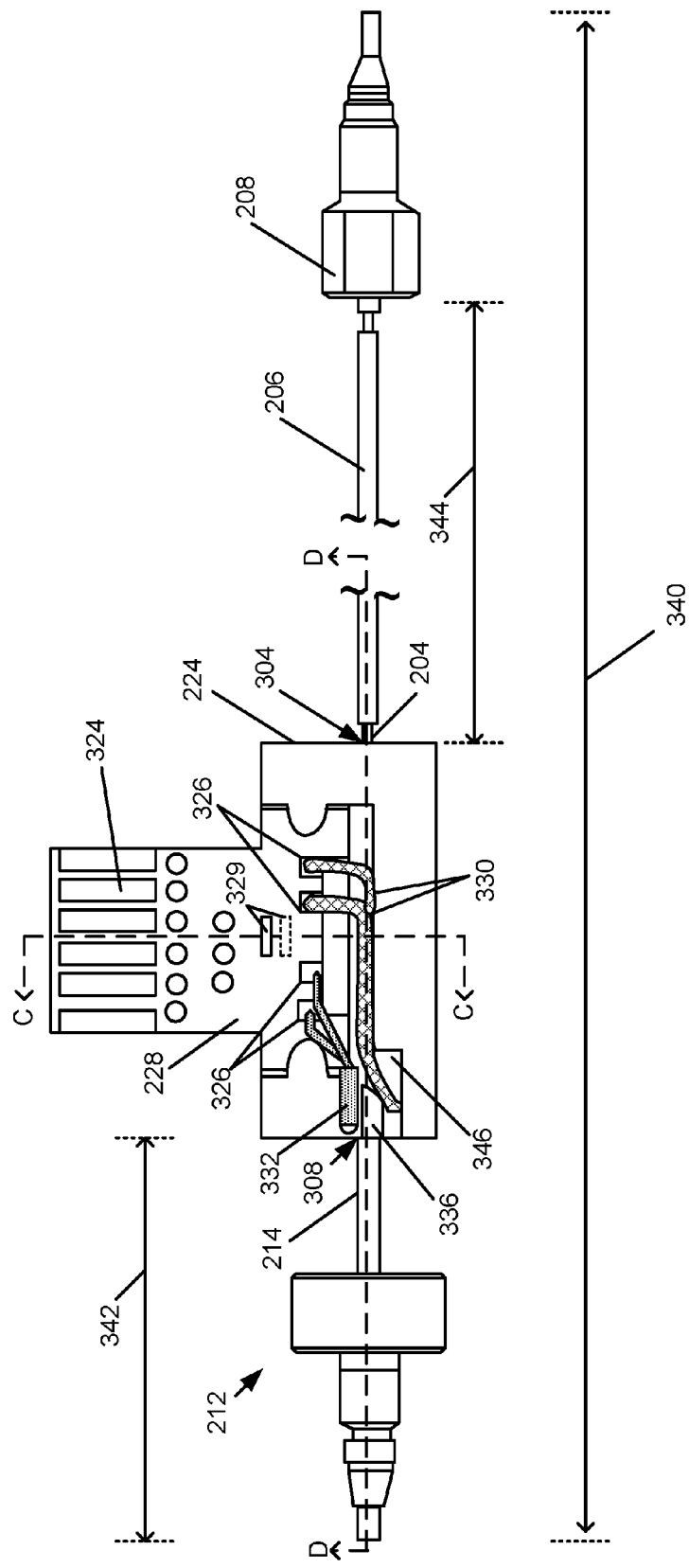
FIG. 15A is an elevated view of the active pre-heater assembly without the spring carrier.
Figure 15B:
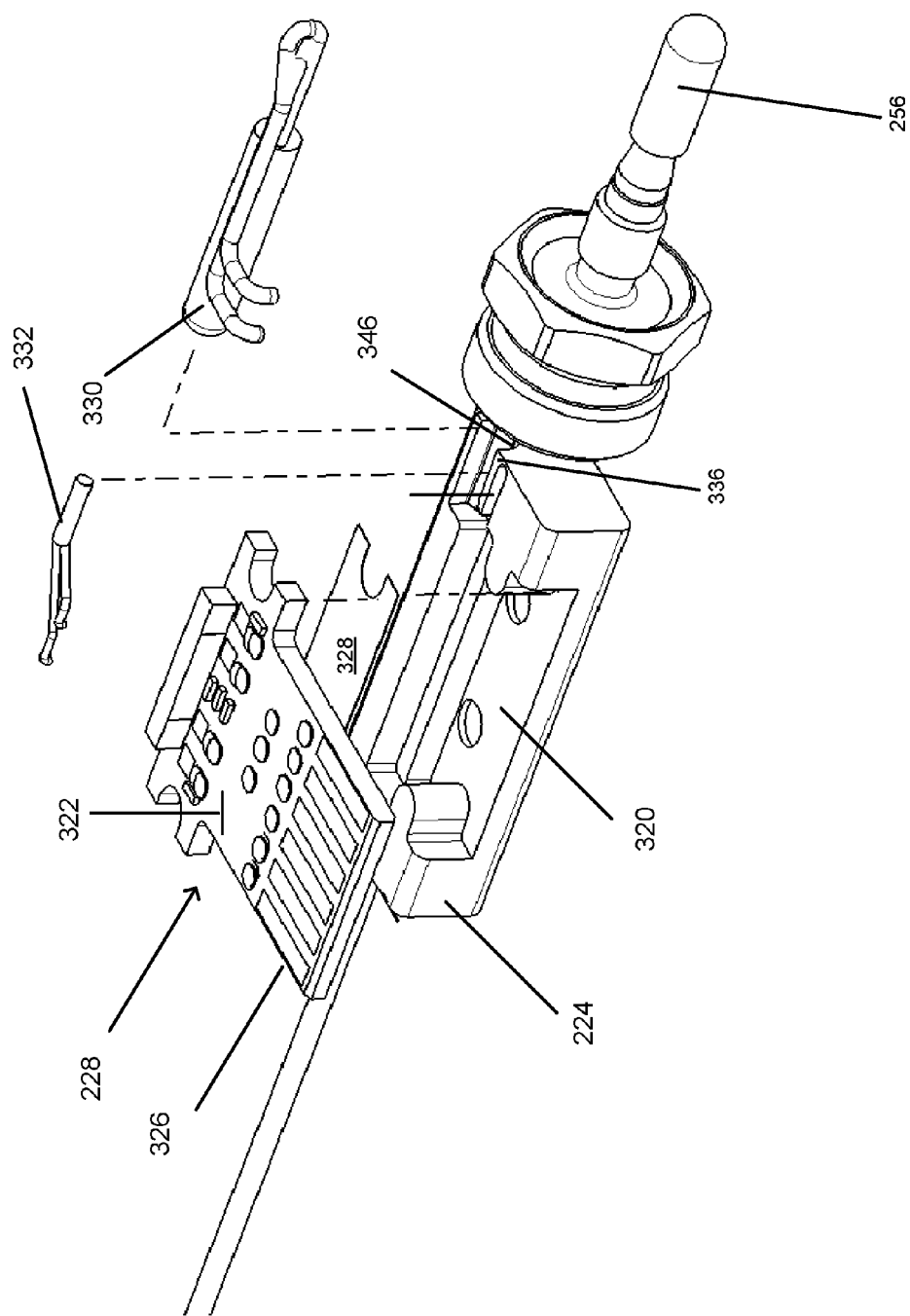
FIG. 15B is an exploded view of the active pre-heater assembly without the spring carrier.

FIG. 15A and FIG. 15B show an embodiment of the active pre-heater assembly 200 without the spring carrier 220 (FIG. 10A). FIG. 15A is an isometric view and FIG. 15B is an exploded view. The heater block 224 has a major cavity 320 (FIG. 15B). The printed circuit board 228 has a contour that fits closely into this cavity 320. An upper surface 322 of the circuit board 228 has contact fingers 324 and electrical contact pads 326. A portion of the printed circuit board 228 with the contact fingers 324 extends from and overlaps the heater block 224. A thin insulation layer 328, also having a contour shaped to fit closely into this major cavity 320, is disposed between the circuit board 228 and the heater block 224, to prevent the circuit board 228 from shorting to the metal heater block 224.

The electronics on the circuit board 228 can include one or more resistors 329 used to detect whether an active pre-heater assembly has been installed in the thermal module 20. In some embodiments, a passive heat exchanger instead of an active pre-heater assembly may be mechanically installed in the heater trough 128. Because the passive heat exchanger operates differently from the active pre-heater, precautions are taken to avoid sending power and control signals designed for operating an active pre-heater to the passive heat exchanger. Before sending such signals, software executing at the sample manager 14 looks for the resistor(s) 329 to ascertain the presence of an active pre-heater in the thermal module.

In addition, the number of resistors 329 on the circuit board 228, and their particular locations on the circuit board, can be used to distinguish among pre-heaters with different wattages, or of different tubing lengths. For instance, in one embodiment the circuit board 228 has two locations for installing such resistors 329. The two locations accommodate four different binary values (i.e., each resistor location represents a binary digit, the presence of a resistor 329 in a given resistor location corresponds to a bit value of '1', and the absence of a resistor 329 in a resistor location corresponds to a bit value of '0'). Thus, in this embodiment, the four possible values represented by the presence or absence of a resistor are 0, 1, 2, and 3 (00b, 01b, 10b, and 11b). The value of 0 corresponds to no pre-heater present in the trough 128, and the values 1, 2, and 3 indicate that a pre-heater is present and can represent different types of pre-heaters and/or tube lengths.

A heater cartridge 330 resides in a cavity 346 in the heater block 224. Two wires of the heater cartridge 330 connect to two of the electrical pads 326 on the upper surface 322 of the circuit board 228. A temperature sensor 332 (preferably, a thermistor) is placed within another cavity 334 of the heater block 224, a thin wall 336 separating the temperature sensor 332 from the heater cartridge 330 to avoid direct contact therewith. Circuitry on the circuit board 228 uses the temperature measured by the temperature sensor 332 to limit the operation of the heater cartridge 330 and thus the maximum temperature reached by the heater block 224. Other circuitry on the circuit board 228 includes a fuse wired in series with the heater cartridge 330, which disconnects the heater cartridge from power in the event of malfunction. An epoxy fills the cavities 320, 334, 346, to cover and protect the heater cartridge, temperature sensor 332, and various electrical components on the circuit board 228.

In one embodiment, the length 340 from one end of the tubing 204 to the other end of the tubing 204 is approximately 12.55 inches; the length 342 from where the tubing 204 enters the heater block 224 and the tip of the column fittings 212 is approximately 1.125 inches; and the length 344 from where the tubing 204 enters the heater block 224 and the tip of the tube fittings 208 is approximately 10 inches.

Figure 15C:
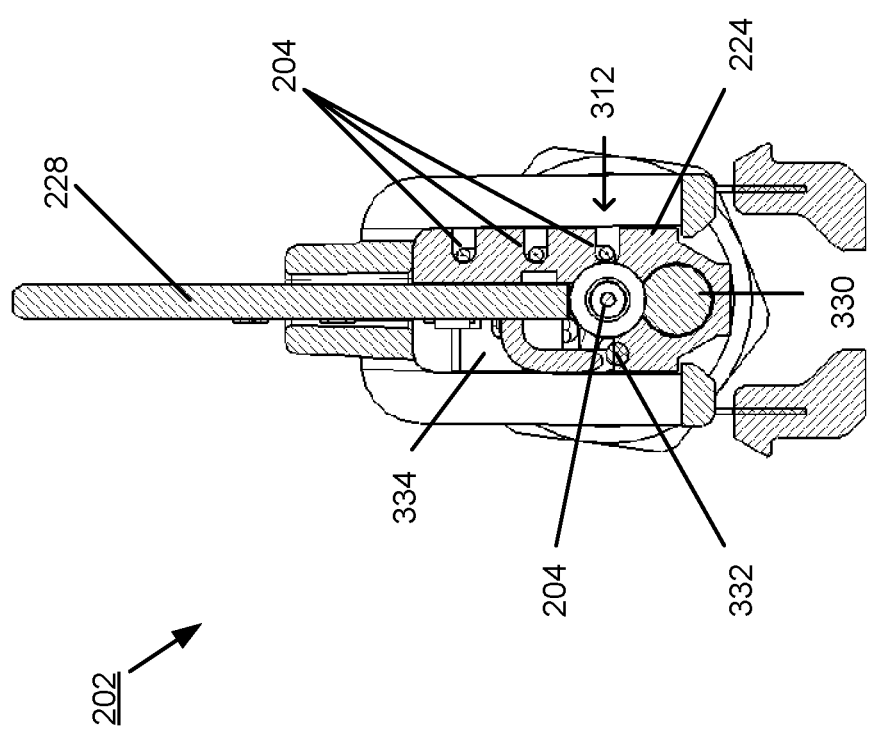
FIG. 15C is a cross-section of the active pre-heater assembly taken along line C-C in FIG. 15A.

FIG. 15C shows a cross-section of the heater block assembly 202 taken along line C-C in FIG. 15A. The cross-section shows the temperature sensor 332 and the heater cartridge 330 amid the heater block 224. The tubing 204 (here, e.g., disposed in the serpentine tube path) is cut thrice in the serpentine tube path by the cross-section.

Figure 15D:
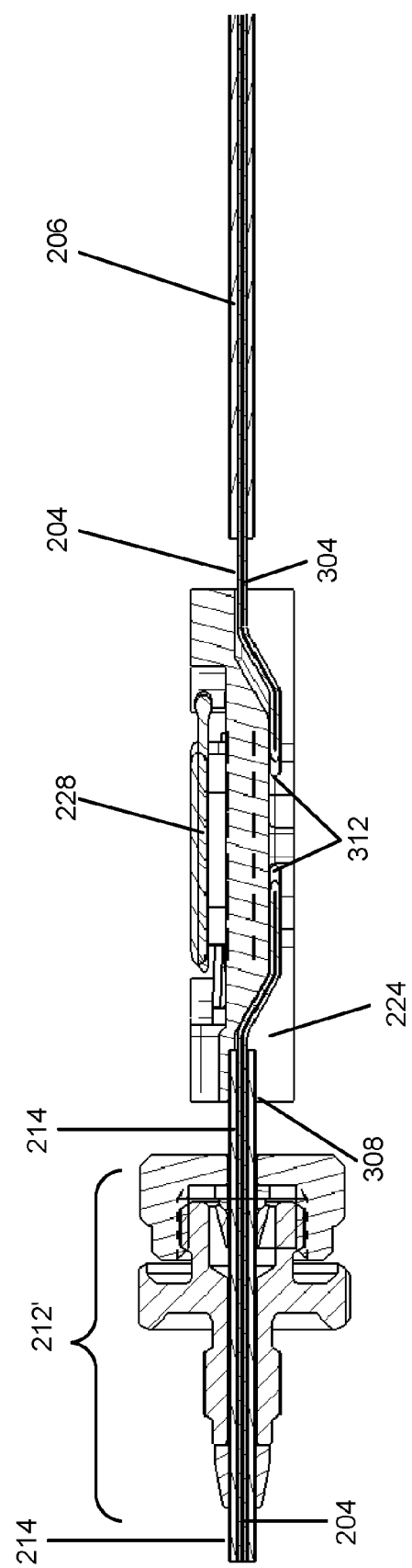
FIG. 15D is a cross-section of the active pre-heater assembly taken along line D-D in FIG. 15A.

FIG. 15D shows a cross-section of the active pre-heater assembly 200 taken along line D-D in FIG. 15A, which passes through the tubing 204. (The column fittings 212' in FIG. 15D correspond to a different embodiment from the column fittings 212 of FIG. 15A). The metal tube sleeve 214 passes entirely through the column fitting 212', enters and is bonded to the tube outlet 308. In one embodiment, the tube sleeve 214 extends approximately 0.125 inches into the tube outlet 308. The tubing 204, itself, takes the serpentine path 312 through the heater block 224 between the tube inlet 304 and the tube outlet 308.

Figure 16:
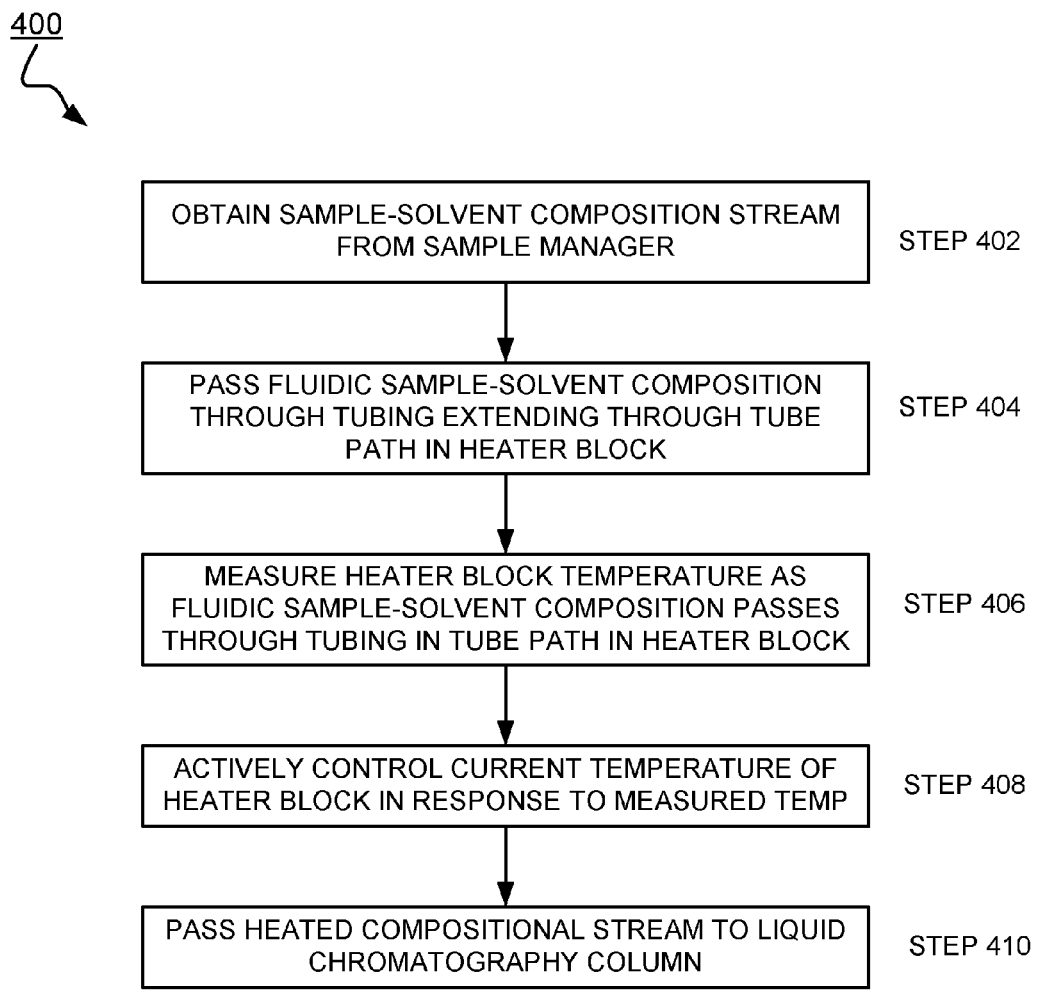
FIG. 16 is a flow diagram of an embodiment of a process of pre-heating a liquid flowing into a liquid chromatography column.

FIG. 16 shows an embodiment of a process 400 of pre-heating a flowing liquid before the liquid enters a liquid chromatography column. At step 402, a sample-solvent composition stream is received. This sample-solvent composition stream is passed (step 404) through tubing extending through a tube path in a heater block assembly. The tubing is in thermally conductive contact with a heater block of the heater block assembly. The heater block is made of thermally conductive material such that heat transfers from the heater block to the sample-solvent composition stream as the sample-solvent composition stream passes through the tubing. A current temperature of the heater block is dynamically measured (step 406) as the sample-solvent composition stream passes through the tubing. The current temperature of the heater block is actively controlled (step 408) in response to the dynamic measurement. The heated sample-solvent composition stream is moved out (step 410) of the heater block into a liquid chromatography column.

Figure 17:
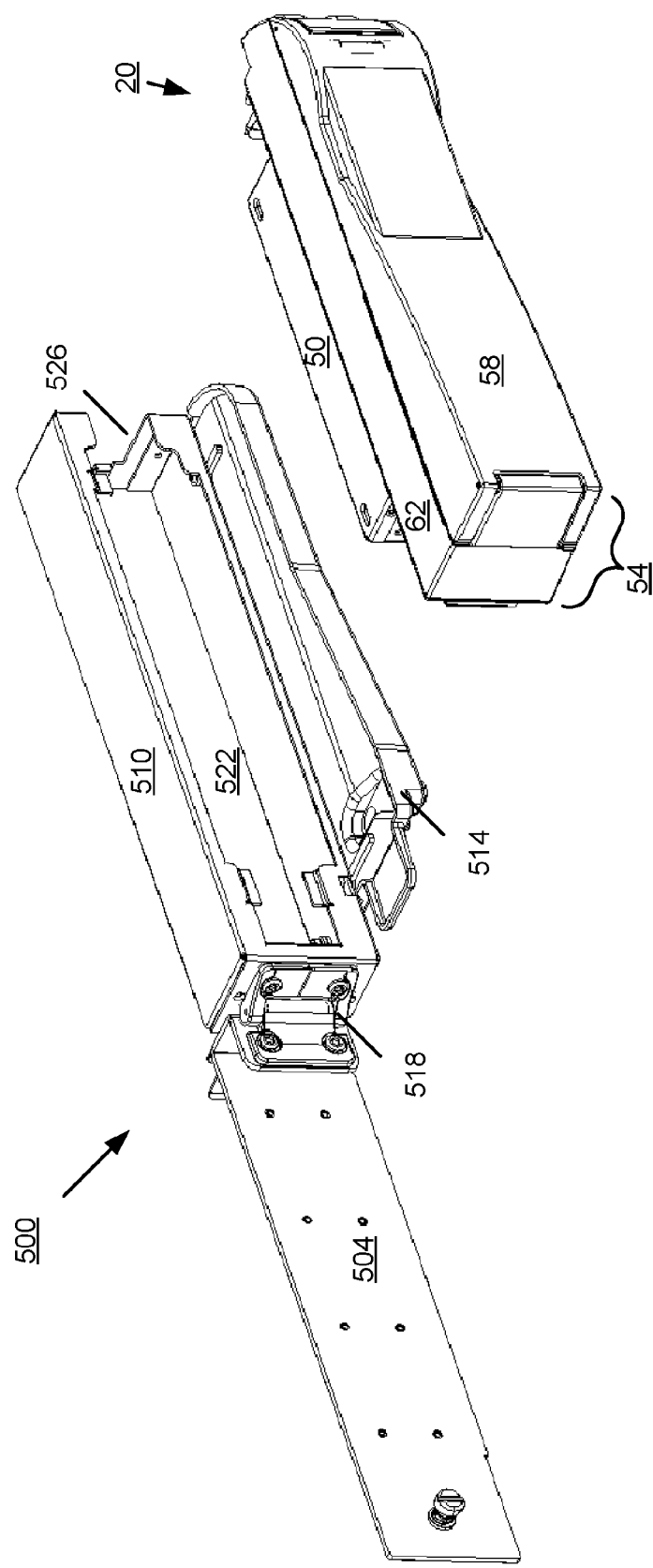
FIG. 17 is an isometric view of an embodiment of a hinge bracket to be used for mounting the thermal module to one side of the column-heater enclosure.
Figure 18:
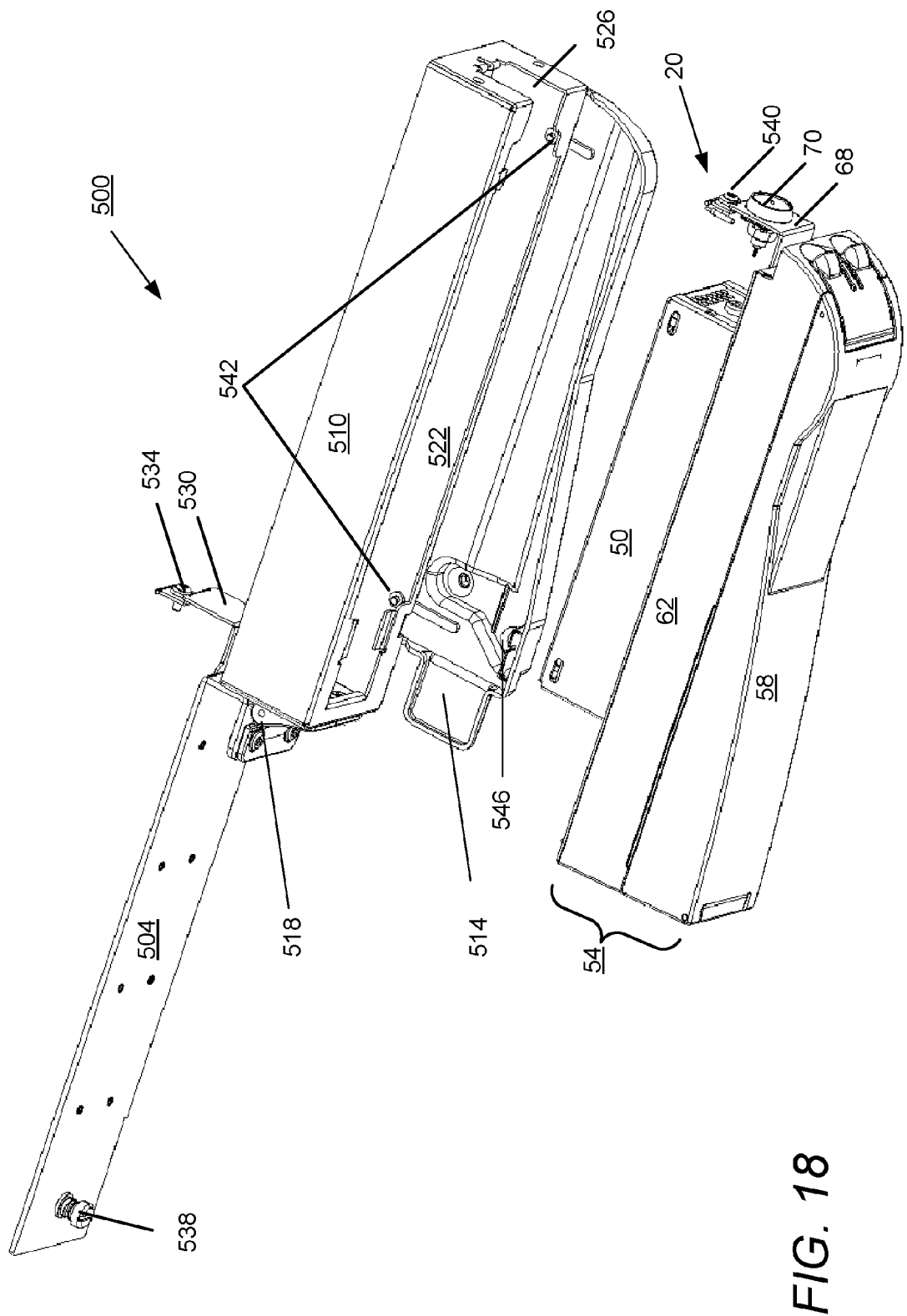
FIG. 18 is a top view of the hinge bracket.

FIG. 17 shows an isometric view of an embodiment of a hinge bracket 500 used for mounting the thermal module 20 to one side of the main housing 30 of the column-heater enclosure 16. The hinge bracket 500 includes an attachment plate 504 and a metal box 510. A drip tray 514 can be attached to the bottom of the metal box 510. A friction hinge 518 connects the attachment plate 504 to one end of the metal box 510. The friction hinge 518 enables the metal box 510 to pivot to any position, relative to the attachment plate 504, between 90° (orthogonal to the front of the plate) and 180° (collinear to the plate). The metal box 510 has an open-faced compartment 522 sized to closely receive the electronics enclosure 50 of the thermal module 20. One end of the compartment 522, opposite the hinge 518, has a cut-out region 526. FIG. 18 shows a top view of the hinge bracket 500. A minor bracket 530 extends from one end of the attachment plate 504. The minor bracket 530 has a fastener 534 used to mount the attachment plate 504 to the side of the main housing 30. Another fastener 538 attaches the other end of the attachment plate 504 to the front of the main housing 30.

The cut-out region 526 at one end of the metal box 510 is sized and shaped to accommodate the bracket 68 of the thermal module 20. A fastener 540 adjacent to the device 70 attaches to the side of the metal box 510, mounting the thermal module 20 to the metal box 510 similar, in this respect, to mounting the attachment plate 534 to the side of the main housing 30. The other end of the thermal module 20 hooks into features at the open face compartment 522 of the metal box 510.

The drip tray 514, attached to the bottom of the metal box 510 by fasteners 542, projects forward of the metal box 510 and slopes downward (in FIG. 18, from right to left) to a drain 546. The direction of drainage is opposite that of the thermal module 20, which in FIG. 18 drains from left to right.

Figure 19:
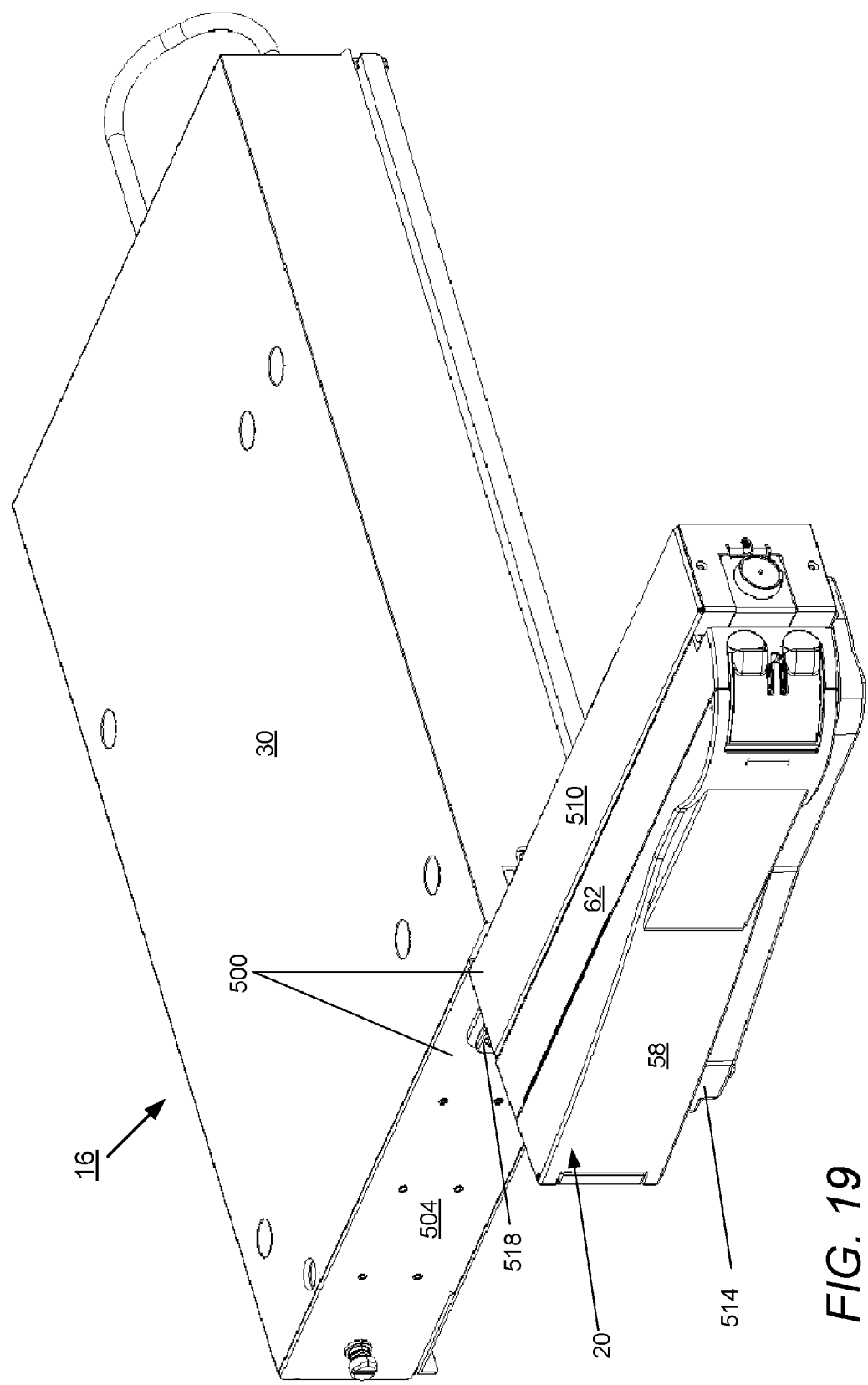
FIG. 19 is an isometric view of the thermal module attached to the column-heater enclosure by the hinge bracket.
Figure 20:
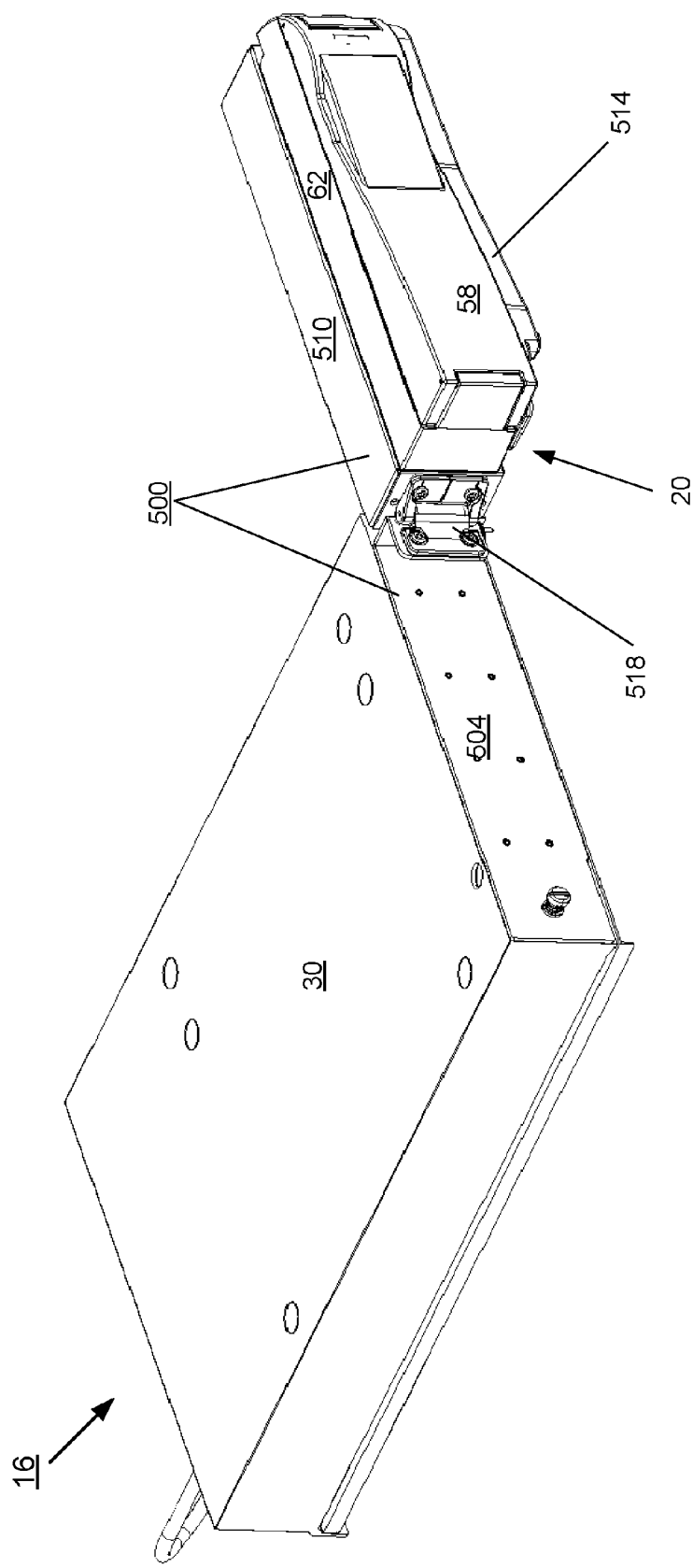
FIG. 20 is another isometric view of the thermal module attached to the column-heater enclosure by the hinge bracket.

FIG. 19 and FIG. 20 show isometric views of the thermal module 20 attached to one side of the main housing 30 by the hinge bracket 500. In each isometric view, the hinge bracket 500 is in the 180° position, with the thermal module 20 extending to the right side of the main housing 20. FIG.

19 shows the thermal module 20 in the foreground, with the drip tray 514 disposed below the column holder 62 for catching leakage flowing down the spout 198 (FIG. 6) in the lower half 180-2 of the trough compartment 120 of the thermal module 20. In FIG. 20, the end of the thermal module 20 is flush (in the same plane) with the end of the metal box 510. When the hinge bracket 500 is in the 90° position, the rear side of the metal box 510 lies in the same plane with the side of the main housing 30.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, RAM, ROM, an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the invention has been shown and described with reference to specific preferred embodiments, it should be understood by those skilled in the art that various changes in form and detail may be made therein without departing from the spirit and scope of the invention.

What is claimed is:

1. An apparatus for heating a liquid in a liquid chromatography system, comprising:
    a heater block assembly including a heater block made of thermally conductive material, the heater block assembly having a tube inlet, a tube outlet, and a tube path between the tube inlet and the tube outlet;
    tubing extending through the tube path from the tube inlet to the tube outlet, the tubing being in thermal communication with the heater block;
    a heater cartridge in thermal communication with the heater block, the heater cartridge configured to provide heat to the heater block for transfer to liquid flowing through the tubing between the tube inlet and the tube outlet of the heater block assembly;

a chromatography column disposed outside the heater block assembly and coupled to an end of the tubing nearest to the tube outlet of the heater block assembly; and circuitry in electrical communication with the heater cartridge to control a temperature of the heater block by controlling operation of the heater cartridge.

2. The apparatus of claim 1, further comprising a temperature sensor in thermal communication with the heater block to provide an indication of the temperature of the heater block, and wherein the circuitry is in electrical communication with the temperature sensor to determine therefrom the temperature of the heater block.

3. The apparatus of claim 1, wherein the tube path between the tube inlet and the tube outlet is serpentine through the heater block assembly.

4. The apparatus of claim 3, wherein a length of the tube path is less than approximately two inches.

5. The apparatus of claim 1, wherein the tube path is entirely linear between the tube inlet and the tube outlet.

6. The apparatus of claim 1, further comprising a column fitting configured to couple the end of the tubing nearest to the tube outlet of the heater block assembly to an inlet port of the liquid chromatography column.

7. The apparatus of claim 6, further comprising a tube fitting configured to couple an opposite end of the tubing nearest to the tube inlet of the heater block assembly to an outlet port of a sample manager.

8. The apparatus of claim 1, wherein the circuitry includes a resistor used by external electronic circuitry to recognize the apparatus.

9. The apparatus of claim 1, wherein the heater block has a first cavity and the heater cartridge is disposed in the first cavity.

10. The apparatus of claim 2, wherein the heater block has a second cavity and the temperature sensor is disposed in the second cavity.

* * * * *